US012747469B2

(12) United States Patent
Kim et al.

(10) Patent No.: US 12,747,469 B2
(45) Date of Patent: Sep. 29, 2026

(54) DNA POLYMERASE VARIANT WITH IMPROVED DISCRIMINATION OF GENETIC VARIANTS

(71) Applicant: GENOTECH CORP., Daejeon (KR)

(72) Inventors: Jae Jong Kim, Daejeon (KR); Si-Kyu Lim, Daejeon (KR); Jeounghyun Ryu, Cheongju-si (KR); Bo Mi Lee, Nonsan-si (KR); Seulki Kim, Daejeon (KR); Sun Ho Cha, Sejong (KR)

(73) Assignee: GENOTECH CORP., Daejeon (KR)

( * ) Notice: Subject to any disclaimer, the term of this patent is extended or adjusted under 35 U.S.C. 154(b) by 975 days.

(21) Appl. No.: 17/928,592

(22) PCT Filed: May 28, 2021

(86) PCT No.: PCT/KR2021/006654

§ 371 (c)(1),
(2) Date: Jun. 15, 2023

(87) PCT Pub. No.: WO2021/242041

PCT Pub. Date: Dec. 2, 2021

(65) Prior Publication Data

US 2023/0304082 A1 Sep. 28, 2023

(30) Foreign Application Priority Data

May 29, 2020 (KR) ........................ 10-2020-0064838
May 27, 2021 (KR) ........................ 10-2021-0068144

(51) Int. Cl.
*C12Q 1/6858* (2018.01)
*C12N 9/12* (2006.01)
*C12Q 1/6848* (2018.01)

(52) U.S. Cl.
CPC ......... *C12Q 1/6858* (2013.01); *C12N 9/1252* (2013.01); *C12Q 1/6848* (2013.01); *C12Q 2600/156* (2013.01)

(58) Field of Classification Search
CPC .................................................... C12N 9/1252
See application file for complete search history.

(56) References Cited

U.S. PATENT DOCUMENTS 5,693,502 A 12/1997 Gold et al.
6,265,193 B1 7/2001 Brandis et al.
8,043,816 B2 10/2011 Astatke et al.
8,759,061 B1 6/2014 Marx et al.
9,267,120 B2 2/2016 Reichert et al.
9,267,130 B2 2/2016 Martin et al.
9,315,787 B2 4/2016 Schafer et al.
9,976,178 B2 5/2018 Mazur et al.
2011/0027833 A1* 2/2011 Hogrefe ............... C12N 9/1252 435/193
2012/0258501 A1 10/2012 Bauer et al.
2013/0034879 A1 2/2013 Skirgaila et al.

FOREIGN PATENT DOCUMENTS

CN 107299091 A 10/2017
CN 109251907 A 1/2019
EP 3 546 576 A1 10/2019
IN 202027003081 A 2/2020
JP 2004-521606 A 7/2004
JP 2005-518223 A 6/2005
JP 2008-506417 A 3/2008
JP 2010-503413 A 2/2010
JP 2019-216723 A 12/2019
KR 10-2019-0007214 A1 1/2019
WO 2009/155464 A2 12/2009
WO 2011157435 A1 12/2011
WO 2015082449 A2 6/2015
WO 2019013451 A1 1/2019

OTHER PUBLICATIONS

Yaukawa et al., "Kinetic analysis of reverse transcriptase activity of bacterial family A DNA polymerases", Biochemical and Biophysical Research Communications, 2012, vol. 427, No. 3, pp. 654-658.*
Schäfers et al., "Complete genome sequence of Thermus brockianus GE-1 reveals key enzymes of xylan/xylose metabolism", Standards in Genomic Sciences (2017) 12:22. DOI 10.1186/s40793-017-0225-7.*
Asakura et al., "Cloning, nucleotide sequence, and expression in *Escherichia coli* of DNA polymerase gene (polA) from thermus thermophilus HB8", Journal of Fermentation and Bioengineering, 1993, vol. 76, Issue 4, pp. 265-269.*
Auton, A. et al., "A global reference for human genetic variation", (2015), Nature 526(7571): 68-74.
Baner, J. et al., "Signal amplification of padlock probes by rolling circle replication", (1998), Nucleic Acids Research 26(22): 5073-5078.
Bergallo, M. et al., "Evaluation of IFN-γ polymorphism +874 T/A in patients with recurrent tonsillitis by PCR Real Time Mismatch Amplification Mutation Assay (MAMA Real Time PCR)" (2015), Cytokine 71(2): 278-282.
Dang, C. and S. D. Jayasena, "Oligonucleotide Inhibitors of Taq DNA Polymerase Facilitate Detection of Low Copy Number Targets by PCR", (1996), J Mol Biol. 264(2): 268-278.
Drum, M. et al., "Variants of a Thermus aquaticus DNA Polymerase with Increased Selectivity for Applications in Allele- and Methylation-Specific Amplification", (2014), PLoS One 9(5): e96640.
Eom, S. H. et al., "Structure of Taq polymerase with DNA at the polymerase active site", (1996), Nature 382(6588): 278-281.
Fa, M. et al., "Expanding the Substrate Repertoire of a DNA Polymerase by Directed Evolution", (2004), J Am Chem Soc 126(6): 1748-1754.

(Continued)

*Primary Examiner* — Suzanne M Noakes
(74) *Attorney, Agent, or Firm* — Sughrue Mion, PLLC

(57) ABSTRACT

The present invention relates to a DNA polymerase variant that belongs to family A, and to a use thereof. The present invention relates to: a DNA polymerase variant which easily undergoes polymerization when the base at the 3'-end of a primer is complementary to a template, and yet has inhibited polymerization when the base at the 3'-end of the primer is non-complementary to the template, and thus facilitates discrimination between the two cases; a PCR process using the variant; and a PCR kit comprising the variant. The present invention is useful for single nucleotide polymorphism analysis (SNP genotyping), somatic mutation detection, and the like.

6 Claims, 10 Drawing Sheets

Specification includes a Sequence Listing.

(56) References Cited

OTHER PUBLICATIONS

Higgins, R. R. et al., "Evaluation and Verification of the Seeplex Diarrhea-V ACE Assay for Simultaneous Detection of Adenovirus, Rotavirus, and Norovirus Genogroups I and II in Clinical Stool Specimens", (2011), Journal of Clinical Microbiology 49(9): 3154-3162.
Holland, P. M. et al., "Detection of specific polymerase chain reaction product by utilizing the 5'- 3' exonuclease activity of Thermus aquaticus DNA polymerase", (1991), Proc Natl Acad Sci U S A 88(16): 7276-7280.
Hritonenko, V. et al. "Omptin proteins: an expanding family of outer membrane proteases in Gram-negative Enterobacteriaceae (Review)" (2007), Molecular Membrane Biology 24(5-6): 395-406.
Ignatov, K. B. et al., "Substitution of Asn for Ser543 in the large fragment of Taq DNA polymerase increases the efficiency of synthesis of long DNA molecules", (1998), FEBS Letters 425(2): 249-250.
Ikebukuro, K. et al. "Screening of DNA aptamers inhibiting Taq DNA polymerase using algorithm mimicking evolution", (2003), Nucleic Acids Research Supplement(3): 309-310.
Jarry, A. et al., "Real-time allele-specific amplification for sensitive detection of the BRAF mutation V600E", (2004), Molecular and Cellular Probes 18(5): 349-352.
Kermekchiev, M. B. et al., "Mutants of Taq DNA polymerase resistant to PCR inhibitors allow DNA amplification from whole blood and crude soil samples", (2009), Nucleic Acids Research 37(5): e40.
Kermekchiev, M. B. et al., "Cold-sensitive mutants of Taq DNA polymerase provide a hot start for PCR", (2003), Nucleic Acids Research 31(21): 6139-6147.
Kim, Y. et al., "Crystal structure of Thermus aquatics DNA polymerase", (1995), Nature 376(6541): 612-616.
Li, Y. et al., "Crystal structures of open and closed forms of binary and ternary complexes of the large fragment of Thermus aquaticus DNA polymerase I: structural basis for nucleotide incorporation", (1998), EMBO J 17(24): 7514-7525.
Lin, Y. and S. D. Jayasena "Inhibition of Multiple Thermostable DNA Polymerases by a Heterodimeric Aptamer", (1997), J Mol Biol 271(1): 100-111.
Loakes, D. et al., "Evolving a polymerase for hydrophobic base analogues", (2009), J Am Chem Soc 131(41): 14827-14837.
Martincorena, I. and P. J. Campbell "Somatic mutation in cancer and normal cells", (2015), Science 349(6255): 1483-1489.
Mhlanga, M. M. and L. Malmberg "Using Molecular Beacons to Detect Single-Nucleotide Polymorphisms with Real-Time PCR", (2001), Methods 25(4): 463-471.
Modeste, E. et al., "A molecular dynamics investigation of the thermostability of cold sensitive I707L KlenTaq1 DNA polymerase and its wild-type counterpart", (2019), J. Chem. Inf. Model. 59(5): 2423-2431.
Nakagawa, H. and M. Fujita "Whole genome sequencing analysis for cancer genomics and precision medicine", (2018), Cancer Sci 109(3): 513-522.
Nazarenko, I. et al., "Whole genome sequencing analysis for cancer genomics and precision medicine" (2002), Nucleic Acids Research 30(9): e37.
Newton, C. R. et al., "Analysis of any point mutation in DNA. The amplification refractory mutation system (ARMS)", (1989), Nucleic Acids Res 17(7): 2503-2516.
Ollis, D. L. et al., "Structure of large fragment of *Escherichia coli* DNA polymerase I complexed with dTMP", (1985), Nature 313(6005): 762-766.
Ong, J. L. et al., "Directed Evolution of DNA Polymerase, RNA Polymerase and Reverse Transcriptase Activity in a Single Polypeptide", (2006), J Mol Biol 361(3): 537-550.
Patel, P. H. and L. A. Loeb "Dna polymerase active site is highly mutable: Evolutionary consequences", (2000), Proc Natl Acad Sci U S A 97(10): 5095-5100.
Poste, G. "Molecular diagnostics: a powerful new component of the healthcare value chain", (2001), Expert Rev Mol Diagn 1(1): 1-5.
Raghunathan, G. and A. Marx "Identification of Thermus aquaticus DNA polymerase variants with increased mismatch discrimination and reverse transcriptase activity from a smart enzyme mutant library", (2019), Sci Rep 9(1): 590.
Reddington, K. et al., "A current overview of commercially available nucleic acid diagnostics approaches to detect and identify human gastroenteritis pathogens", (2014), Biomol Detect Quantif 1(1): 3-7.
Schechter, I. and A. Berger "On the Size of the Active Site in Proteases. | Papain", (2012), Biochem Biophys Res Commun 425(3): 497-502.
Schultz, H. J. et al., "Taq DNA Polymerase Mutants and 2'-Modified Sugar Recognition", (2015), Biochemistry 54 (38): 5999-6008.
Sherrill, C. B. et al., "Nucleic Acid Analysis Using an Expanded Genetic Alphabet to Quench Fluorescence", (2004), J Am Chem Soc 126(14): 4550-4556.
Strerath, M. et al., "Directed DNA Polymerase Evolution: Effects of Mutations in Motif C on the Mismatch-Extension Selectivity of Thermus aquaticus DNA Polymerase", (2007), Chembiochem 8(4): 395-401.
Suzuki, M. et al., "Thermus aquaticus DNA Polymerase | Mutants with Altered Fidelity Interacting Mutations in the O- Helix*", (2000), J Biol Chem 275(42): 32728-32735.
Jehara, H. et al., "Detection of Telomerase Activity Utilizing Energy Transfer Primers: Comparison with Gel- and ELISA-Based Detection", (1999), Biotechniques 26(3): 552-558.
Whitcombe, D. et al., "Detection of PCR products using self-probing amplicons and fluorescence", (1999), Nat Biotechnol 17(8): 804-807.
Wu, E. Y. et al., "A Conservative Isoleucine to Leucine Mutation Causes Major Rearrangements and Cold Sensitivity In KlenTaq1 DNA Polymerase", (2015), Biochemistry 54(3): 881-889.
Yamagami, T. et al., "Mutant Taq DNA polymerases with improved elongation ability as a useful reagent for genetic engineering", (2014), Front Microbiol 5: 461.
Zhang, K. et al., "Haplotype Block Partitioning and Tag SNP Selection Using Genotype Data and Their Applications to Association Studies", (2004), Genome Res 14(5): 908-916.
International Search Report dated Sep. 15, 2021 in International Patent Application No. PCT/KR2021/006654.
Written Opinion dated Sep. 15, 2021 in International Patent Application No. PCT/KR2021/006654.
Kim, et al., "Six Germline Genetic Variations Impair the Translesion Synthesis Activity of Human DNA Polymerase K", Chemical Research in Toxicology, Oct. 17, 2016, vol. 29, No. 10, pp. 1-33 (33 pages).

* cited by examiner

FIG. 1

Pol A

```
                                   Ha                Loop                Hb
                                   490          500          510          520
                                   |            |            |            |
T. aquaticus            AGHPFNLNSRDQLERVLFDELGLPAIGKTEKTGKRSTSAAVLEALREAHPIVEKILQYR  a.a. 479-536 of SEQ ID NO: 1
T. sp. Z05              AGHPFNLNSRDQLERVLFDELRLPALGKTQKTGKRSTSAAVLEALREAHPIVEKILQHR  a.a. 481-538 of SEQ ID NO: 2
T. maritima             AGEPFNINSPKQVSRILFEKLGIKPRGKTTKTGDYSTRIEVLEELAGEHEIIPLILEYR  SEQ ID NO: 101
E. coli                 AGEEFNLSSTKQLQTILFEKQGIKP-LKKTPGGAPSTSEEVLEELALDYPLPKVILEYR  SEQ ID NO: 102
B. caldotenax           AGQEFNINSPKQLGVILFEKLQLPVLKKSKTG--YSTSADVLEKLAPYHEIVENILQHY  SEQ ID NO: 103
G. stearothermophilus   AGQEFNINSPKQLGTVLFDKLQLPVLKKTKTG--YSTSADVLEKLAPHHEIVEHILHYR  SEQ ID NO: 104
                        **. **:.* .*:  :**::  :    *.      **   *** *   : :   **.:
                        conserved            less conserved          conserved
```

【Fig.5】
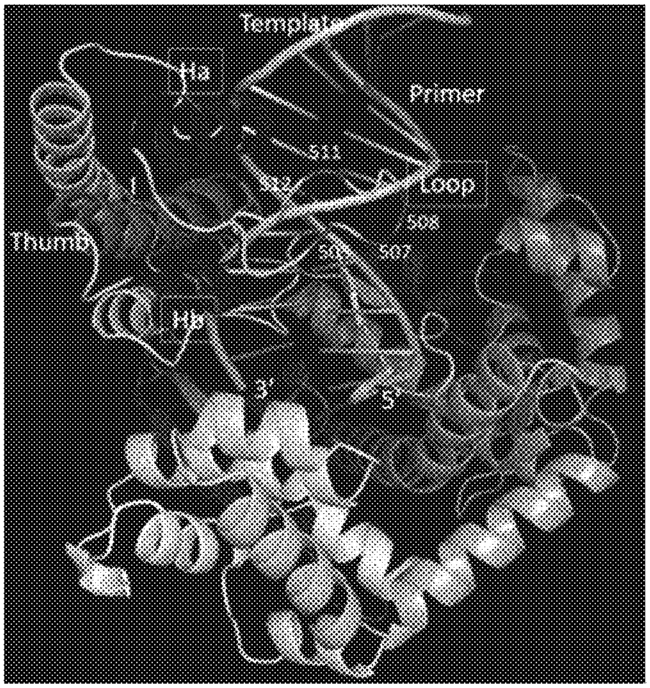
【Fig.6】
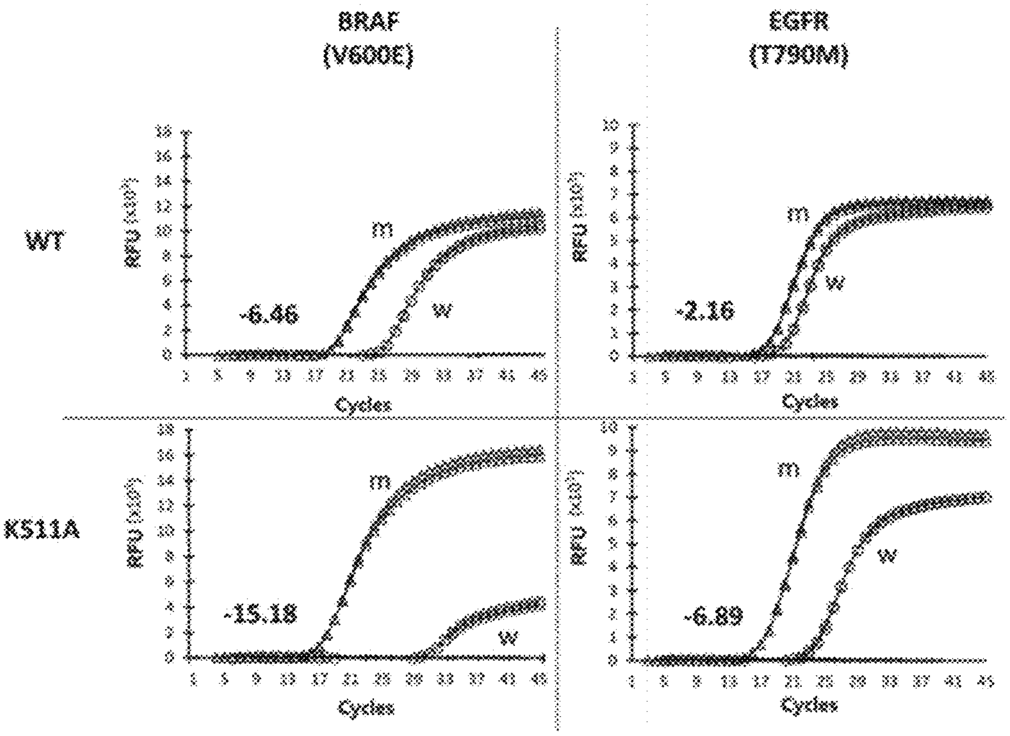

【Fig.7a】
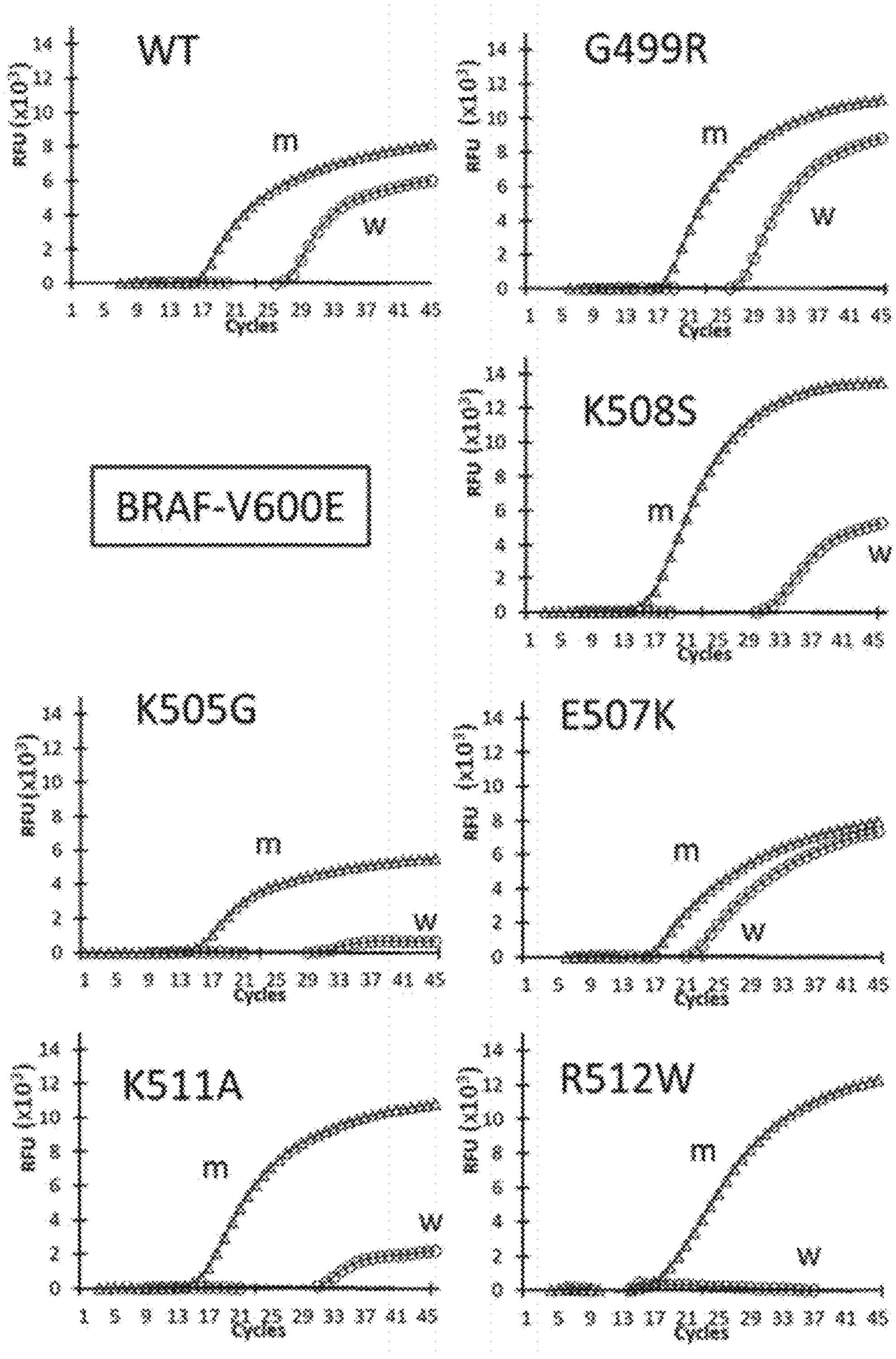

【Fig.7b】
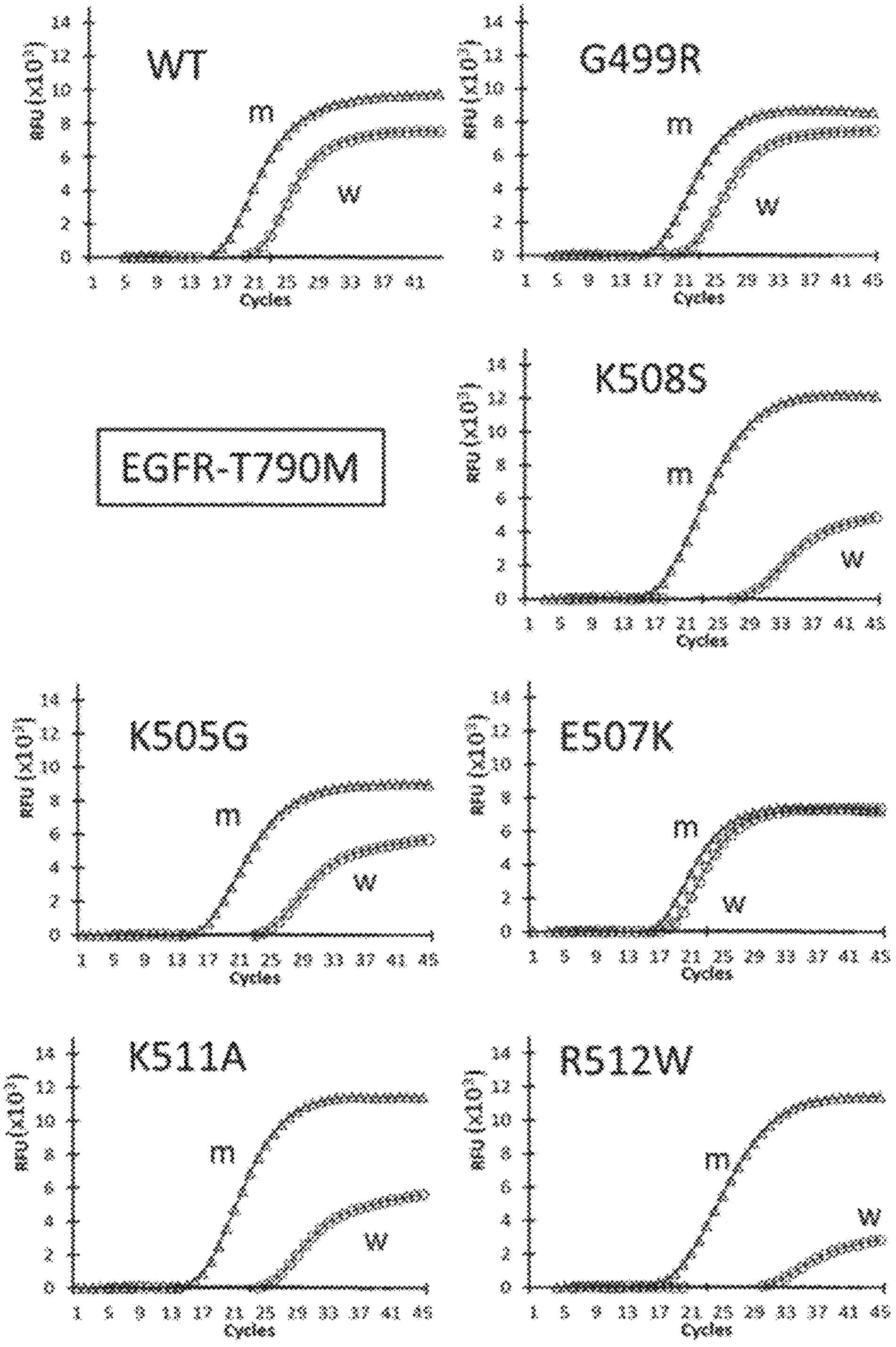

【Fig.8】
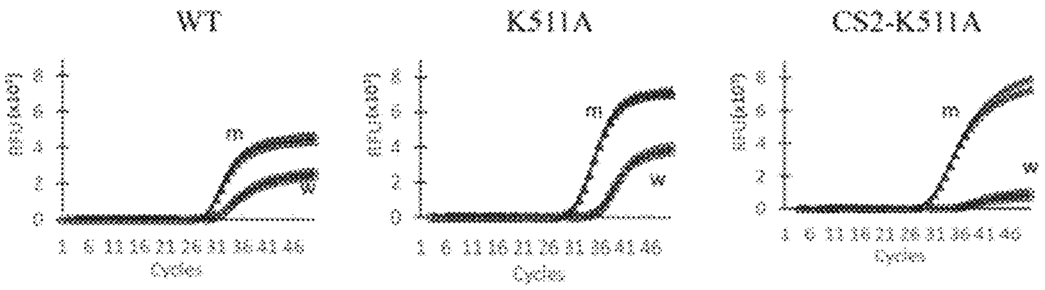

DNA POLYMERASE VARIANT WITH IMPROVED DISCRIMINATION OF GENETIC VARIANTS

CROSS REFERENCE TO RELATED APPLICATIONS

This application is a National Stage of International Application No. PCT/KR2021/006654 filed May 28, 2021, claiming priority based on Korean Patent Application No. 10-2020-0064838 filed May 29, 2020 and Korean Patent Application No. 10-2021-0068144 filed May 27, 2021.

SEQUENCE LISTING

The present application contains a Sequence Listing which has been submitted electronically in an ASCII text file and is hereby incorporated by reference in its entirety. The ASCII text file, created Mar. 27, 2026, is named Q319324SUBSEQLIST20260327.txt and is 37,291 bytes in size.

TECHNICAL FIELD

The present invention relates to a DNA polymerase mutant belonging to family A and use thereof and, specifically, to a DNA polymerase mutant, a PCR method using the mutant, and a PCR kit containing the mutant, wherein the mutant facilitates the discrimination between matched and mismatch pairings of primer 3'-terminal bases and a template by allowing smooth polymerization when the primer 3'-terminal bases are matched with the template and inhibiting polymerization when mismatched. The present invention is useful for single polynucleotide polymorphism (SNP) genotyping, somatic mutation detection, and the like.

BACKGROUND ART

Identifying genetic mutations involved in the traits of various living organisms including humans, drug metabolisms, immunological responses, diseases, such as hereditary diseases and such as cancer, that is, genetic mutations, such as single nucleotide polymorphism, addition, and deletion, is very important in the implementation of precision medicine, such as prediction of treatment, determination of treatment methods, prognosis of treatment, and observation of recurrence (Auton, Brooks et al. 2015, Zhang, Qin et al. 2004, Poste 2001, Nakagawa and Fujita 2018, Martincorena and Campbell 2015). In addition, the identification or discrimination of genetic mutations is very useful for breeding and selection of species, determination of origins and varieties, and the like in the agricultural food field.

Genetic mutations may be inherent in living organisms or may occur due to environmental or endogenous causes during growing. Single nucleotide polymorphism (SNP) is one of the most common genetic mutation types in the human body and others. In the following description, SNPs as exemplified by various genetic mutations are described.

Among the methods that are used for the determination of SNPs in living things including humans, one of the most common, economical, and convenient methods is a gene amplification technique utilizing a polymerase, that is, polymerase chain reaction (PCR), and in particular, quantitative real-time PCR ("qPCR") or "real-time PCR" that can measure the amount of genetic mutations in real time during PCR is useful. Real-time PCR, which is a qualitative and quantitative detection technique for nucleic acids, has been applied in various fields such as health, agriculture, food, and environments. The real-time PCR developed in the early 1990s has been developing into a more accurate and precise technique by continuously overcoming technical limitations.

In the development of gene determination kits using real-time PCR, the generation of non-specific signals and the low discrimination between mutant and wild-type gene sequences are considered typical technical limitations of real-time PCR.

Especially, non-specific signals are necessarily regulated to develop the real-time PCR technique as a diagnostic technique for cancer and pathogen detection. False positives due to non-specific signals lower the reliability of tests, and especially in diagnostic techniques, such as non-invasive or minimally invasive liquid biopsy requiring the detection of very small amounts, methods for improving PCR efficiency and specificity are needed for accurate diagnosis of a small amount of target mutation. To improve PCR efficiency and specificity, methods for developing compositions to be added to PCR solutions, designing special probes or primers, or enzyme engineering have been sought.

As for the compositions to be added to PCR solutions, research has been made mainly on additive compositions for increasing PCR reactivity, producing primer dimers, producing non-specific PCR products generated by binding of used primers to non-specific targets, or eliminating PCR efficiency reduction by high GC ratios and specific high-order structures. Such compositions are dimethylsulfoxide (DMSO), betaine, and the like.

Lots of methods for preventing non-specific amplification by blocking reactions performed at low temperatures and performing PCR at high temperatures have been reported for so-called HotStart PCR. Among the methods, a method for adding DNA polymerase (DNAP)-specific monoclonal antibodies [Biotechniques (1994) 16(6):1134-1137], a method for adding single-stranded oligonucleotides inhibiting the activity of DNA polymerase, so-called aptamers, [US/005693502A (1997) (Gold and Jayasena 1997); J. Mol. Biol. 271:100-111 (1997) (Lin and Jayasena 1997); and Nucleic Acids Research Supplement No. 3: 309-310 (2003) (Ikebukuro and Noma 2003)], or a method for inhibiting non-specific DNA synthesis by using double-stranded nucleotides that have the binding ability with DNA polymerase at low temperatures and inhibit the activity of DNA polymerase but not inhibit the activity of DNA polymerase by forming no double helix under PCR conditions above a specific temperature [J. Mol Biol. 264(2):268-278 (1996) (Dang and Jayasena 1996); U.S. Pat. No. 8,043,816 B2 (2011) (Astatke, Chatterjee et al. 2011)] has been known as a HotStart PCR method.

In methods of improving PCR efficiency and specificity by using special probes and/or primers, the special probes and primers are for specifically detecting amplified target products, and a method of using a probe with high specificity has been developed. The use of DNA-binding fluorophores, such as SYBR green I or SYTO9 in real-time PCR results in the detection of the overall amplified products, often causing non-specific signals. Target sequence specific probes were developed to solve the problems, and examples of such probes are TaqMan probe (dual labelled signaling hydrolysis probe) [P Natl Acad Sci USA 88, 7276-280 (1991) (Holland, Abramson et al. 1991)], molecular beacons [Methods. 25, 463-71 (2001) (Mhlanga and Malmberg 2001)], scorpion probes [Nat Biotechnol. 17, 804-07 (1999) (Baner, Nilsson et al. 1998)], light upon extension (LUX) primers [Nucleic acids research. 30, e37 (2002) (Nazarenko, Lowe et al.

2002)], amplifluor primers [BioTechniques. 26, 552-58 (1999) (Uehara, Nardone et al. 1999)], and the like.

In addition, there was developed a method of using primers or special oligonucleotide blockers with high specificity for selectively amplifying target mutant genes. Examples of the method of using primers with high specificity are methods, such as amplification refractory mutation system PCR (ARMS-PCR) wherein an additional mutant sequence in addition to one mutant sequence is added to the 3'-terminal on the basis of allele specific PCR (AS-PCR) for discrimination by a difference of one base at the 3'-terminal [Mol Cell Probes. 18. 349-352 (2004) (Jarry, Masson et al. 2004); Nucleic Acids Res 17. 2503-2516 (1989) (Newton, Graham et al. 1989); Nat Biotechnol. 17. 804-807 (1999) (Whitcombe, Theaker et al. 1999); Cytokine 71, 278-282 (2015) (Bergallo, Gambarino et al. 2015)]. In recent years, SeeGene's dual-priming oligonucleotide (DPO) [J. Am. Chem. Soc. 126, 4550-4556 (2004) (Sherrill, Marshall et al. 2004); Biomol. Detect. Quantif. 1 3-7 (2014) (Reddington, Tuite et al. 2014); J. Clin. Microbiol. 49. 3154-3162 (2011) (Higgins, Beniprashad et al. 2011)] and Swift Biosciences's myT primer (as described on the Swift Biosciences website swiftbiosci.com/technology/myt-primers), which are methods of using primers composed of two separate regions so as to maintain the mismatch discrimination between a template and a primer while increasing annealing stability, have been developed.

Numerous DNA polymerases have been developed for easy use in PCR for inhibiting non-specific signals or enhancing allele discrimination. Thermophilic DNA polymerases are usually used in PCR techniques.

DNA polymerases are classified into seven or more families, but thermophilic polymerases used in the PCR techniques are mainly selected from a thermophilic bacteria-derived enzyme group including Taq DNA polymerase belonging to family A and archaea-derived enzyme group including Pfu DNA polymerase belonging to family B. Out of these, the family A DNA polymerases including Taq DNA polymerase generally have 5'→3'-nuclease activity, and the 5'→3'-nuclease activity includes both exonuclease activity and endonuclease activity, wherein the endonuclease activity site is also referred to as flap endonuclease 1 (FEN1). This activity is very important for the release of a specific signal through the degradation of a hydrolysis probe (e.g., TaqMan probe). Taq DNA polymerase has no 3'→5' exonuclease activity, and thus is very suitable for PCR using a primer, of which the 3'-terminal is mismatched with the template DNA. For allele-specific (AS) primers or amplification refractory mutation system (ARMS) primers with mismatched 3'-terminals, the amplification efficiency of a mutant gene, a wild-type gene, or the two alleles are determined according to the matched or mismatched primer 3'-bases, with relatively favorable clinical outcomes resulting therefrom. For some cases, however, amplification occurs in part even with 3'-mismatched primers, occasionally causing discrimination errors in highly sensitive diagnosis for detecting small amount (copies) of mutant DNA incorporated into high amount (copies) of wild-type DNA.

A Taq DNA polymerase having the amino acid sequence of SEQ ID NO: 1 is widely used for real-time PCR for molecular diagnosis. Unless otherwise stated below, the amino acid sequence of the DNA polymerase follows SEQ ID NO: 1.

```
(wild-type Taq DNA polymerase)
                                                 SEQ ID NO: 1
MRGMLPLFEPKGRVLLVDGHHLAYRTFHALKGLTTSRGEPVQAVYGFAKS

LLKALKEDGDAVIVVFDAKAPSFRHEAYGGYKAGRAPTPEDFPRQLALIK

ELVDLLGLARLEVPGYEADDVLASLAKKAEKEGYEVRILTADKDLYQLLS

DRIHVLHPEGYLITPAWLWEKYGLRPDQWADYRALTGDESDNLPGVKGIG

EKTARKLLEEWGSLEALLKNLDRLKPAIREKILAHMDDLKLSWDLAKVRT

DLPLEVDFAKRREPDRERLRAFLERLEFGSLLHEFGLLESPKALEEAPWP

PPEGAFVGFVLSRKEPMWADLLALAAARGGRVHRAPEPYKALRDLKEARG

LLAKDLSVLALREGLGLPPGDDPMLLAYLLDPSNTTPEGVARRYGGEWTE

EAGERAALSERLFANLWGRLEGEERLLWLYREVERPLSAVLAHMEATGVR

LDVAYLRALSLEVAEEIARLEAEVFRLAGHPFNLNSRDQLERVLFDELGL

PAIGKTEKTGKRSTSAAVLEALREAHPIVEKILQYRELTKLKSTYIDPLP

DLIHPRTGRLHTRFNQTATATGRLSSSDPNLQNIPVRTPLGQRIRRAFIA

EEGWLLVALDYSQIELRVLAHLSGDENLIRVFQEGRDIHTETASWMFGVP

REAVDPLMRRAAKTINFGVLYGMSAHRLSQELAIPYEEAQAFIERYFQSF

PKVRAWIEKTLEEGRRRGYVETLFGRRRYVPDLEARVKSVREAAERMAFN

MPVQGTAADLMKLAMVKLFPRLEEMGARMLLQVHDELVLEAPKERAEAVA

RLAKEVMEGVYPLAVPLEVEVGIGEDWLSAKE
```

Taq DNA polymerase is a thermophilic enzyme belonging to Family A, which includes *E. coli* DNA polymerase I. Taq DNA polymerase is divided into a 5'-nuclease domain (1-288 aa) as a small fragment and a polymerase domain (289-832) as a large fragment (Stoffel fragment or KlenTaq), and the polymerase domain of Taq DNA polymerase can bind well with the DNA duplex structure by forming a human right-handed structure through palm, finger, and thumb sub-domain (Ollis, Brick et al. 1985) (Kim, Eom et al. 1995) (Eom, Wang et al. 1996).

There have been mutation studies on various amino acid residues considering the positions of binding sites and active sites of primers, probes, NTP, and Mg++, through numerous crystal structure studies on DNA polymerase I. Main search regions are motif A region (residues 605-617) (Patel and Loeb 2000) (Suzuki, Yoshida et al. 2000), 0-helical region (residues 659-671) (Suzuki, Yoshida et al. 2000), Pa-helical region of the finger domain (residues 704-707) (Kermekchiev, Tzekov et al. 2003), a nucleotide binding pocket region (residues 611-617), the steric gate related amino acid residue (residue 615), the third β-sheet region (residues 597-609) of the palm domain (Ong, Loakes et al. 2006), motif C region (Strerath, Gloeckner et al. 2007), and P'-domain region (residues 704-717) (Kermekchiev, Kirilova et al. 2009).

Through a lot of studies about such regions, mutants with increased enzymatic activity (Ignatov, Miroshnikov et al. 1998), cold sensitive variants available for hot start PCR (Kermekchiev, Tzekov et al. 2003) (Wu, Walsh et al. 2015) (Modeste, Mawby et al. 2019), mutants with extended availability for various substrates, such as rNTPs and hydrophobic base analogues, to be usable for reverse transcription PCR, bisulfite PCR, error prone PCR, and the like (Suzuki, Yoshida et al. 2000) (Ong, Loakes et al. 2006) (Strerath, Gloeckner et al. 2007) (Loakes, Gallego et al. 2009) (Schultz, Gochi et al. 2015) (Fa, Radeghieri et al. 2004) (Loakes, Gallego et al. 2009) [U.S. Pat. No. 9,267,130B2 (2016) (Martin, Simpson et al. 2016)] US2012/0258501 A1

(Bauer, Myers et al. 2012), mutants with enhanced elongation ability (Yamagami, Ishino et al. 2014), mutants exhibiting resistance to PCR inhibition by components contained in various samples, such as blood and soil (Kermekchiev, Kirilova et al. 2009), and the like were developed.

In addition to the above, polymerases with enhanced ability to discriminate between matches and mismatches in the 3'-terminal sequences of allele or mutation-specific primers have been reported (PLos One. 9(5): e96640 (2014) (Drum, Kranaster et al. 2014) (Raghunathan and Marx 2019); KR 10-2017-0088373 (2017) (Lee, Byeongcheol 2017); U.S. Pat. No. 0,034,879A1 (2013) (Skiragaila, Tubeleviciute et al. 2013); WO 082449A2 (2015) (Marx, drum et al. 2015); U.S. Pat. No. 9,267,120 B2 (2016) (Reichert, Bauer et al. 2016); U.S. Pat. No. 8,759,061 B1 (Marx, Summerer et al. 2014) Chembiochem 8 (4) 395-401 (2007) (Strerath, Gloeckner et al. 2007)).

In these studies, mutations were intensively secured for amino acid residues that were presumed to be structurally binding to primers, templates, and nucleotides entering enzymes, and surprising results were obtained. Especially, K508W, R536K, R587K, R660V mutants (Drum, Kranaster et al. 2014) and Mut_ADL variants (mutation sites N483K, E507K, S515N, K540G, A570E, D578G, V586G, and I614M) (Raghunathan and Marx 2019) showed high discrimination, and the activity thereof was also relatively comparable to that of wild-type Taq DNA polymerase, and these are evaluated to have sufficient commercial applicability.

However, mutants for polymerases have been developed for more than 20 years, but the development of polymerases with high discrimination has not been successful except for the above studies. The reason is that efficient library construction strategies (CSR, spCSR, phage display), very easy mutant production and selection systems, such as direct evolution, have been developed, but the setting of the selection pressure or screening system, such as selection of highly resistant enzymes using the addition of inhibitors or selection of enzymes capable of using noncanonical substrates or the like was not very useful for the selection of enzymes with high discrimination.

Thus, selecting enzymes through rational targets mutation is very important for increasing the possibility of selecting enzymes with excellent discrimination. Therefore, the finding of structural regions of polymerases, which are associated with discrimination, can ensure the development of enzymes with excellent discrimination.

DISCLOSURE OF INVENTION

Technical Problem

As for the detection of mutant genes in specimens, such as living tissues, blood, feces, and saliva, among clinical samples for cancer diagnosis and others, mutant DNA is very difficult to specifically detect since a large number of wild-type DNA sequences in addition to a trace amount of mutant DNA are incorporated in the specimens. There is a need to ensure specificity with which mutations incorporated into many wild types and present at trace amounts of less than 1% can be detected, and high robustness is needed for clinical application. Especially, low false positives for wild-type sequences and high specificity for mutant sequences need to be ensured. For such reasons, for the improvement of PCR efficiency and specificity to be suitable for high-sensitivity diagnosis, such as cancer diagnosis, methods for developing compositions to be added to PCR solutions, designing special probes and/or primers, or modifying enzymes have been sought.

The addition of reagents, such as DMSO and betaine, for improving amplification efficiency, monoclonal antibodies for DNA polymerase inhibition, or oligonucleic acids, so-called aptamers, for inhibiting DNA polymerase activity at low temperatures, such as room temperature, often improves DNA amplification efficiency and inhibits non-specific PCR product amplification or primer dimer formation. However, the addition of these reagents makes it difficult to enhance the discrimination of alleles.

Moreover, discriminating, especially, single nucleotide polymorphisms through the use of specific primers and probes is not technically easy, has limitations in universal application, and requires a lot of efforts and costs for designing specific primers or probes.

One of the most accessible and efficient way to date is to enhance the discrimination of alleles by using AS primer or ARMS primer to discriminate alleles through the presence or absence of 3'-mismatches due to mutation sequences of the alleles. The use of AS primer with one mismatched base shows a low discrimination of alleles in spite of high PCR efficiency, and the use of ARMS primer with two or more mismatched bases shows better discrimination of alleles compared with the use of AS primer, but results in low PCR amplification efficiency, often causing deterioration of limit of detection (LOD).

Therefore, studies have been continuing to improve the detection specificity of mutant sequences by using mutant DNA polymerases with enhanced discrimination between 3'-mismatches and 3'-matches, but no very successful mutants have been obtained so far despite many efforts. Moreover, selected mutant DNA polymerases were not commercially available since the enzyme activity was frequently reduced and the detection sensitivity was also degraded.

For efficient detection of alleles or mutant sequences, the development of polymerases is continuously required capable of enhancing the discrimination between matches and mismatches between a primer 3'-terminal and template DNA that are used, even without deterioration of enzyme activity.

Accordingly, the present invention has been made to solve the above-described problems, and an aspect of the present invention is to provide a DNA polymerase with excellent discrimination in order to effectively detect genetic mutations, such as SNPs, More specifically, an aspect of the present invention is to provide a DNA polymerase mutant for enhancing the discrimination between mismatches and matches between a template and a primer 3'-terminal, specifically, to provide a family A DNA polymerase, and more specifically, to provide a thermophilic DNA polymerase including Taq DNA polymerase.

Furthermore, an aspect of the present invention is to provide a PCR method and a PCR kit using the DNA polymerase mutant.

Solution to Problem

To obtain DNA polymerase mutants with high discrimination, the present inventors ensured excellent mutants by defining a mutation target region in an enzyme and intensively constructing and exploring various mutants for the region.

Through the invention, the present inventors intend to provide a DNA polymerase showing a surprising level of genetic mutation discrimination or allele discrimination.

One region explored in the present invention is a region belonging to the loop region (497-514, hereinafter loop region) between Ha (487-496) and Hb (515-521) (Kim, Eom et al. 1995) (Li, Korolev et al. 1998), which correspond to the tip of the thumb domain (FIG. 1). This loop region has few negatively charged amino acids and many positively charged amino acids and thus shows a high pI value. This region differs from the loop region of *T. sp.* Z05 DNA polymerase (Z05) (SEQ ID NO: 2), known as an enzyme with high discrimination between matches and mismatches in terms of only three amino acids (R501, L505, and Q509).

```
(TZ05 DNA polymerase)
                                        SEQ ID NO: 2
MKAMLPLFEPKGRVLLVDGHHLAYRTFFALKGLTTSRGEPVQAVYGFAKS

LLKALKEDGYKAVFVVFDAKAPSFRHEAYEAYKAGRAPTPEDFPRQLALI

KELVDLLGFTRLEVPGFEADDVLATLAKKAEREGYEVRILTADRDLYQLV

SDRVAVLHPEGHLITPEWLWEKYGLKPEQWVDFRALVGDPSDNLPGVKGI

GEKTALKLLKEWGSLENILKNLDRVKPESVRERIKAHLEDLKLSLELSRV

RSDLPLEVDFARRREPDREGLRAFLERLEFGSLLHEFGLLEAPAPLEEAP

WPPPEGAFVGFVLSRPEPMWAELKALAACKEGRVHRAKDPLAGLKDLKEV

RGLLAKDLAVLALREGLDLAPSDDPMLLAYLLDPSNTTPEGVARRYGGEW

TEDAAHRALLAERLQQNLLERLKGEEKLLWLYQEVEKPLSRVLAHMEATG

VRLDVAYLKALSLELAEEIRRLEEEVFRLAGHPFNLNSRDQLERVLFDEL

RLPALGKTQKTGKRSTSAAVLEALREAHPIVEKILQHRELTKLKNTYVDP

LPGLVHPRTGRLHTRFNQTATATGRLSSSDPNLQNIPIRTPLGQRIRRAF

VAEAGWALVALDYSQIELRVLAHLSGDENLIRVFQEGKDIHTQTASWMFG

VSPEAVDPLMRRAAKTVNFGVLYGMSAHRLSQELAIPYEEAVAFIERYFQ

SFPKVRAWIEKTLEEGRKRGYVETLFGRRRYVPDLNARVKSVREAAERMA

FNMPVQGTAADLMKLAMVKLFPHLREMGARMLLQVHDELLLEAPQARAEE

VAALAKEAMEKAYPLAVPLEVEVGIGEDWLSAKG

(Loop region of wild-type Taq DNA
polymerase)
                                        SEQ ID NO: 7
497-ELGLPAIGKTEKTGKRST-514
```

This loop region (residues 497-514 or positions corresponding thereto) may be selected from a part of a DNA polymerase, and more specifically a part of the amino acid sequence constituting a family A DNA polymerase.

The α-helices Ha and Hb regions of Taq DNA polymerase are somewhat sequence-conserved regions (80% or more), sequence-conserved regions (90% or more), or highly sequence-conserved regions (95% or more) in the polymerase family A, and the loop region (residues 497-514 of wild-type Taq DNA polymerase or positions corresponding thereto) is present between the two helices, and this region may be selected for the purpose of the present invention.

The loop region explored in the present invention is associated with DNA binding as shown in the examples of the present invention.

This loop region is associated with the non-degradation of DNA polymerase during the binding of DNA and DNA polymerase as shown in the examples of the present invention.

This loop region is associated with the non-degradation of DNA polymerase at a high KCl concentration, that is, at a KCl concentration of 200 mM or higher, as shown in the examples of the present invention.

As shown in the examples of the present invention, the degradation of Taq DNA polymerase or mutants thereof is inhibited by DNA, so that it can be seen that the loop region is associated with DNA binding, more specifically, primer binding.

As a result of studying polymerase structures, the loop region is predicted to be a binding region between Taq DNA polymerase and a primer as a substrate, as shown in the examples of the present invention.

As embodied in one example of the present invention, a Taq DNA polymerase mutant (e.g., "K511A" mutant) constructed by a mutation in this region was shown to enhance the PCR discrimination between a 3'-match and a 3'-mismatch, indicating that the loop region presented in the present invention is associated with primer binding.

It has not been reported prior to the present application that residues 497-514 of the wild-type Taq DNA polymerase or a loop region at positions corresponding thereto, presented in the present invention is associated with primer binding.

The present inventors employed the loop region to improve or lower substrate specificity of a DNA polymerase, which is the purpose of the present invention.

Improving substrate specificity means that depending on whether a primer 3'-terminal base is matched or mismatched with a template in the binding between the template and the primer, the addition of a 3'-matched primer, compared with the addition of a 3'-mismatched primer, allows PCR to be performed more effectively and/or lowers errors during polymerization.

On the contrary, lowering substrate specificity may mean, for example, facilitating the use of pseudo-substrates, such as rNTP and hydrophobic base analogues, or modified substrates, besides the normal substrates dNTPs, and/or increasing polymerization errors.

The present inventors provide a loop region for the present invention to select mutants with enhanced PCR discrimination between when a primer 3'-terminal base is matched with a template and when the primer 3'-terminal base is mismatched with the template, which one of the main purpose of the present invention.

The term "discrimination" recited in the description, examples, and claims of the present invention refers to discriminating genetic mutations or allele mutations, such as SNPs, present in target gene sequences from normal genes, and specifically to a difference in the degree of amplification of a target gene in real-time PCR between when the template of the normal gene or mutant gene is matched with a primer 3'-terminal base and when mismatched. The difference in the degree of amplification may be determined by electrophoresis after PCR or may be determined by a difference in Ct (or Cq) value between a 3'-match and a 3'-mismatch (ΔCt=Ct value of the 3'-mismatch−Ct value of the 3'-match) by real-time PCR or the like.

In an embodiment of the present invention, the purpose of the present invention can be achieved by substituting an original amino acid with another amino acid, with respect to one or more amino acids selected from the amino acids constituting the loop region (residues 497-514 of wild-type Taq DNA polymerase or a region corresponding thereto).

An embodiment of the present invention shows that the purpose of the present invention can be achieved through a plurality of representative amino acid mutations in this loop region.

An embodiment of the present invention shows that the purpose of the present invention can be achieved by substituting an amino acid, selected among polar amino acids belonging to the loop region (residues 497-514 of wild-type Taq DNA polymerase or a region corresponding thereto), with another amino acid. Specifically, the polar amino acids may be selected from the positively charged amino acid residues arginine (Arg or R), histidine (His or H), and lysine (Lys or K), or the negatively charged amino acid residues aspartic acid (Asp or D) and glutamic acid (Glu or E).

More specifically, the purpose of the present invention can be achieved by a substitution of an amino acid selected from K505, E507, K508, K511, and R512 in Taq DNA polymerase.

Also, as for other thermophilic DNA polymerases belonging to family A, DNA polymerases mutants with enhanced discrimination can be produced by selecting a region corresponding to the loop region (SEQ ID NO: 7) of Taq DNA polymerase. As a specific example, as for the Z05 DNA polymerase (SEQ ID NO: 2), a polymerase mutant can be produced by selecting a loop region (499-517) as a region corresponding to the loop region (497-514) of Taq DNA polymerase.

More specifically, a mutant can be produced by a substitution of at least one amino acid selected from an amino acid region corresponding to the loop region (499-517), preferably R501, K507, K510, K513, and R515, which are charged amino acids belonging to the loop region, in Z05 DNA polymerase (SEQ ID NO: 2). Q509 of the Z05 DNA polymerase, corresponding to E507 of Taq DNA polymerase, may also be a target of substitution.

The mutation of a polymerase refers to the change of, after the selection of at least one amino acid from a sequence of a series of amino acids constituting the polymerase, an amino acid present in the original sequence to another amino acid selected from the other 19 amino acids that are naturally used by a living organism (excluding the original amino acid among 20 amino acids), or the mutation of a polymerase includes chemical or enzymatic alteration (e.g., glycosylation, amination, acylation, hydroxylation, etc.), deletion, or addition. In the present invention, the mutation of a polymerase refers to a substitution of the original amino acid with one amino acid among the other 19 amino acids in nature. The 20 amino acids in nature are alanine (Ala or A), arginine (Arg or R), asparagine (Asn or N), aspartic acid (Asp or D), cysteine (Cys or C), glutamine (Gln or Q, glutamic acid (Glu or E), Glycine (Gly or G), Histidine (His or H), Isoleucine (Ile or I), Leucine (Leu or L), Lysine (Lys or K), Methionine (Met or M), Phenylalanine (Phe) or F), proline (Pro or P), serine (Ser or S), threonine (Thr or T), tryptophan (Trp or W), tyrosine (Tyr or Y), and valine (Val or V).

The mutation of a DNA polymerase for achieving the purpose of the present invention may be typically attained by changing the gene sequence coding the polymerase. The triple codon sequences of changed amino acids do not limit the present invention.

Furthermore, as for the mutation of a DNA polymerase for achieving the purpose of the present invention, the techniques expressing the DNA polymerase do not limit the scope of the present invention. For example, protein expression, types of cloning vectors, types of promoters for expression, tagging to facilitate purification (His tag, etc.), optimizing the gene sequence for host cells, types of host cells (bacteria, yeast, algae, invertebrate animal cells (insects), plant cells, mammalian cells, and in-vitro translation systems, etc.), and the like do not limit the scope of the present invention just for being different from those in the specific examples of the present invention.

Furthermore, the methods for obtaining a DNA polymerase mutant for achieving the purpose of the present invention do not limit the present invention. For example, devices, buffers, resin types, column types, and specific methods such as precipitation and filtration, for chromatography do not limit the present invention just for being different from those in the specific examples of the present invention.

In addition, the primers described in the examples of the present invention are merely illustrative of the present invention and do not limit the scope of the present invention.

In the present invention, the primers for PCR include an allele specific primer (AS primer) or an amplification refractory mutation system (ARMS) primer.

The term "3'-mismatch" used herein refers to a mismatch between a primer 3'-terminal and a template, and indicates that one or more bases among seven bases or five bases in the primer 3'-terminal are mismatched with the template (or a target gene), and more specifically includes a case where the last base of the primer 3'-terminal is mismatched with a base of the template.

The term "3'-match" used herein refers to a complementary match between a primer 3'-terminal and a template (or a target gene), and includes a case where the last base of the primer 3'-terminal is matched with a base of the template.

The DNA polymerase in the present invention is preferably an enzyme belonging to the polymerase family A (*E. coli* Pol I family). This polymerase may be selected from DNA polymerases originated from thermophilic bacteria, preferably thermophilic eubacteria, and more preferably DNA polymerases originated from the genus Thermos, the genus *Thermotoga*, the genus *Thermococcus*, the genus Deinococcus, and the genus *Bacillus*. The DNA polymerases can also be applied to several biotechnological methods including PCR.

The purpose of the present invention can be achieved through the mutation in a loop region of a DNA polymerase or a region corresponding thereto.

More specifically, the purpose of the present invention can be achieved through the mutation of the loop region (residues 497-514) of Taq DNA polymerase and the mutation in a corresponding loop region of a family A DNA polymerase.

The purpose of the present invention can be achieved by a mutation of at least one uncharged amino acid through the mutation in the loop region (497-514) of Taq DNA polymerase or a loop region corresponding thereto of a family A DNA polymerase.

The purpose of the present invention can be achieved by a mutation of at least one charged amino acid through the mutation in the loop region (497-514) of Taq DNA polymerase or a loop region corresponding thereto of a family A DNA polymerase.

The purpose of the present invention can be achieved by a mutation of at least one positively charged amino acid through the mutation in the loop region (497-514) of Taq DNA polymerase or a loop region corresponding thereto of a family A DNA polymerase.

The purpose of the present invention can be achieved by a substitution of K at position 505 of Taq DNA polymerase or an amino acid corresponding thereto in a loop region of a family A DNA polymerase.

The purpose of the present invention can be achieved by a substitution of E at position 507 of Taq DNA polymerase or an amino acid corresponding thereto in a loop region of a family A DNA polymerase.

The purpose of the present invention can be achieved by a substitution of R at position 508 of Taq DNA polymerase or an amino acid corresponding thereto in a loop region of a family A DNA polymerase.

The purpose of the present invention can be achieved by a substitution of K at position 511 of Taq DNA polymerase or an amino acid corresponding thereto in a loop region of a family A DNA polymerase.

The purpose of the present invention can be achieved by a substitution of R at position 512 of Taq DNA polymerase or an amino acid corresponding thereto in a loop region of a family A DNA polymerase.

The mutation tested as one example of the present invention is G499R, K505G, K505I, K505L, K505M, K505F, E507G, E507K, E507Q, K508A, K508S, K508R, K511A, K511R, R512K, R512W, or the like. Preferably, a mutant with high mutation discrimination is a K505G, K505I, K505L, K505M, K505F, K508A, K508S, K508R, K511A, K511R, R512K, or R512W mutation Taq DNA polymerase, in which a positively charged amino acid is substituted with another amino acid.

The reason why the purpose of the invention is achieved by these enzymes will be described as follows.

The advantages and inventiveness of the present invention can be explained by the relationship between mutant activity and structure in the loop region of the present invention and the electrostatic interaction correlation of amino acids in the primer and the loop region.

A mutation region according to an example of the present invention is the loop region (497-514; SEQ ID NO: 7) of Taq DNA polymerase (SEQ ID NO: 1) or a loop region corresponding thereto of a family A DNA polymerase. Such a loop region is a DNA binding region. A region cleaved by the *E. coli* protease (OmpT), described in an example of the present invention, is this loop region, and the cleavage of this region by the protease is inhibited during the binding of this loop region and DNA, so that it was confirmed in the present invention that this loop region is a DNA binding region.

Surprisingly, this loop region is present between Ha (487-496) and Hb (515-521) (Kim, Eom et al. 1995) (Li, Korolev et al. 1998) corresponding to the tip of the thumb domain (FIG. 1), which were not intensively explored for the alteration of DNA polymerases, and this region is predicted to bind to the phosphate backbone of a primer.

The region intensively explored in an example of the present invention is a loop region (497-514) between Ha (487-496) and Hb (515-521) in Taq DNA polymerase.

This region is associated with the binding with a DNA primer as shown in the examples of the present invention.

The binding region of a primer for DNA polymerization has been considered as a target of mutation for developing an enzyme for discriminating between a 3'-match and a 3'-mismatch, which is one of the main purposes of the present invention.

The intensive exploration of the loop region in the present invention provides a very important way for the development of new enzymes with enhanced discrimination between matches and mismatches of a primer 3'-terminal base and template DNA.

In an example of the present invention, an amino acid residue as a target of mutation may be preferentially selected from the positively charged amino acid residue arginine (Arg or A), histidine (His or H), or lysine (Lys or K), or the negatively charged amino acid residue aspartic acid (Asp or D) or glutamic acid (Glu or E) in the loop region (497-514) between Ha (487-496) and Hb (515-521).

As for these amino acid residues, the charged amino acid residues play a very important role in determining the binding ability between a DNA polymerase and DNA, especially, a primer. Therefore, at least one mutation of these amino acids can change the binding ability of DNA, especially, a primer to an enzyme, thereby enhancing the discrimination and/or improving PCR amplification activity and/or changing substrate specificity.

A negatively charged amino acid present or newly introduced in this loop region can interfere with the binding between the loop and the phosphate backbone of the DNA primer, thereby reducing the activity of the DNA polymerase.

A positively charged amino acid present or newly introduced in this loop region can facilitate the binding between the loop region and the phosphate backbone of the DNA primer, thereby improving the activity of the DNA polymerase.

An enzyme having excellent discrimination and maintained DNA polymerase activity can be produced by a substitution of a positively charged amino acid present in the loop region with an uncharged amino acid.

Advantageous Effects of Invention

According to the present invention, a DNA polymerase mutant with enhanced discrimination of base matches or mismatches between a template and a primer while having maintained or improved polymerase activity is provided by an amino acid mutation in a loop region between Ha and Hb domains of family A thermophilic DNA polymerases including Taq DNA polymerase.

Such a DNA polymerase mutant is used in real-time PCR and thus is useful for single nucleotide polymorphism (SNP) genotyping, somatic mutation detection, and the like.

Furthermore, such a DNA polymerase mutant can be used for a PCR kit to enhance the discrimination.

BRIEF DESCRIPTION OF DRAWINGS

FIG. 1 illustrates DNA polymerase regions binding to primers and containing densely located amino acids. The loop region (residues 497-514) and adjacent regions of Taq DNA polymerase are compared among the DNA polymerase regions of *T. aquaticus, T. sp* Z05, *T. maritima, E. coli, B. caldotenax, G. stearothermophilus.*

FIG. 2A shows the degradation results of wild-type Taq DNA polymerase expressed in *E. coli* MV1184. The red arrows indicate protein bands resulting from the degradation. The DEAE column chromatography purification product was washed with buffer A to remove KCl. S represents a wild-type Taq DNA polymerase standard product. 0, no filtering; 1×, filtering once; 2×, filtering twice; S, standard Taq DNA Polymerase. FIG. 2B shows an SDS-PAGE image of samples obtained by filtering a DEAE column chromatography purification product of a Taq DNA polymerase mutant containing E507K mutation expressed in *E. coli* MV1184 with buffer A containing 0, 100, 300, and 500 mM KCl. FIG. 2C shows an SDS-PAGE image of samples obtained by mixing a DEAE column chromatography purification product of a Taq DNA polymerase mutant containing E507K mutation expressed in *E. coli* MV1184 with 0, 0.4, 2.0, 10, and 50 μg of salmon sperm DNA or with a collection of fractions (BP) after the elution of Taq DNA polymerase on DEAE column chromatography, followed by filtering with buffer A. M, protein molecular weight marker; C, non-treatment test group; BP, samples mixed with BP.

Figure 3:
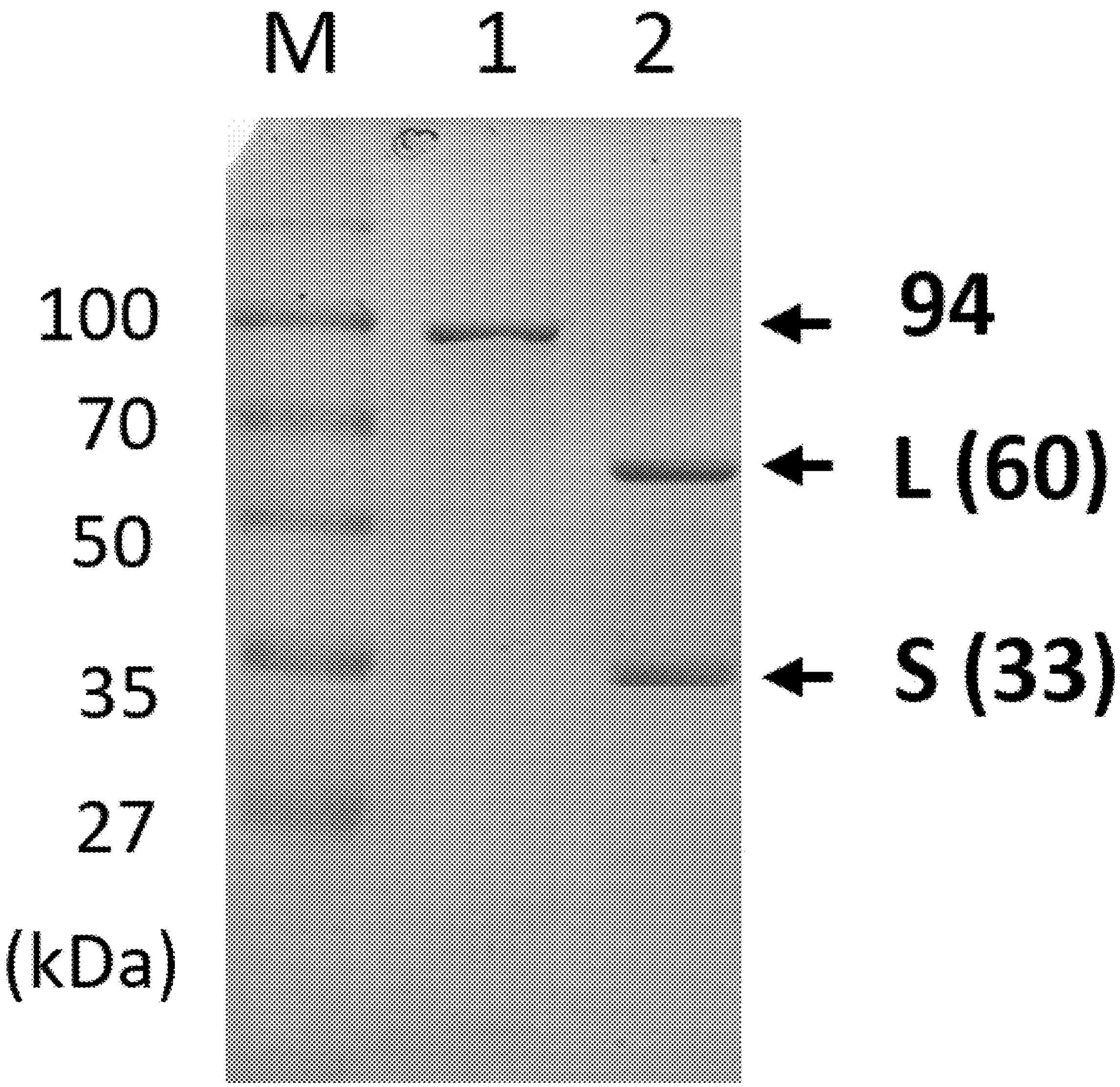

FIG. 3 illustrates an SDS-PAGE image of a Taq DNA polymerase degradation product. 1: non-treatment group, 2: degradation treatment group.

Figure 4:
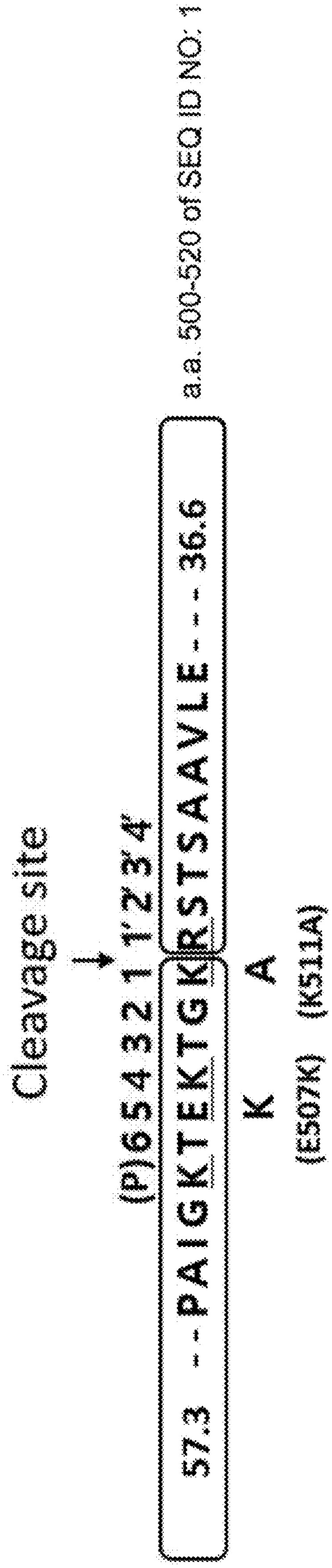

FIG. 4 is a schematic diagram showing the Taq DNA polymerase cleavage site and OmpT recognition site (P).

FIG. 5 is a schematic diagram showing a close-contact structure between DNA and the loop structure of Taq DNA polymerase. α-helix Ha (residues 487-496, blue region), α-helix Hb (residues 515-521, blue region), α-helix I (residues 527-552, purple region), and loop (residues 497-514, a region between the two blue regions) in the thumb subdomain of Taq DNA polymerase, uncharged amino acid residues (green region), the numbers representing amino acid residue positions in Taq DNA polymerase.

FIG. 6 illustrates real-time PCR results using the K511A Taq DNA polymerase mutant and the wild-type Taq DNA polymerase. Normal DNA (w) and mutant DNA (m) of BRAF-V600E and EGFR-T790M were used as templates. Each number represents the value obtained by subtracting the Ct value of real-time PCR using mutant DNA from the Ct value of real-time PCR using normal DNA. WT: results obtained by using the wild-type Taq DNA polymerase, K511A: results obtained by using the K511A mutation Taq DNA polymerase.

FIGS. 7A and 7B illustrate real-time PCR results for determining the discrimination of Taq DNA polymerase mutants containing typical mutations of respective sites. BRAR-V600E and EGFR-T790M, which were samples crudely purified from *E. coli* BL21 (DE3) strain in which respective mutant proteins were expressed, were tested for mutation discrimination. WT represents the results obtained by using wild-type Taq DNA polymerase, and G499R, K505G, E507K, K508S, K511A, and R512W represent the results obtained by using corresponding Taq DNA polymerase mutants, respectively.

FIG. 8 illustrates real-time PCR results using CS2-K511A and K511A Taq DNA polymerase mutants and wild-type Taq DNA polymerase. Normal DNA (w) and mutant DNA (m) of EGFR-T790M were used as templates. EGFR-ARMS-F was used as the forward primer. WT: wild-type Taq DNA polymerase, K511A: K511A mutation Taq DNA polymerase, CS2-K511A: CS2-K511A mutation Taq DNA polymerase

BEST MODE FOR CARRYING OUT THE INVENTION

The present invention is directed to a DNA polymerase mutant containing at least one amino acid mutation in a loop region between Ha and Hb sequences in a DNA polymerase having homology of at least 80% with the Taq DNA polymerase consisting of SEQ ID NO: 1 or a Klenow fragment thereof, wherein the DNA polymerase mutant has maintained polymerization activity and enhanced discrimination of an allelic or genetic mutation compared with a wild-type DNA polymerase.

The mutation may be an amino acid substitution, insertion, or deletion.

The loop region may be present at positions 497-514 in SEQ ID NO: 1 or at positions corresponding thereto.

An amino acid at at least one position selected from the group consisting of positions 497, 498, 499, 500, 501, 502, 503, 505, 506, 509, 510, 511, 512, 513, and 514 in SEQ ID NO: 1 or positions corresponding thereto may be mutated.

The mutant may further contain, in addition to the above mutation, at least one mutation of I707L and E708K or at least one mutation at positions corresponding thereto.

The DNA polymerase having homology of at least 80% may have homology of at least 90%, at least 91%, at least 92%, at least 93%, or at least 94%, and mores preferably homology of at least 85%, at least 95%, or at least 97%, with the Taq DNA polymerase consisting of SEQ ID NO: 1.

At least one of charged amino acids present at positions 497, 505, 511, and 512 in SEQ ID NO: 1 or positions corresponding thereto may be mutated.

At least one of positively charged amino acids present at positions 505, 511, and 512 or positions corresponding thereto may be mutated.

At least one amino acid present at positions 504, 507, 508, 707, and 708 or positions corresponding thereto may be further mutated in addition to the above amino acid mutation position.

The mutant may contain at least one mutation selected from G499R, K505G, K505I, K505L, K505M, K505F, E507A, E507G, E507S, E507R, E507Q, K508A, K508G, K508S, K511A, K511S, R512K, and R512W or corresponding mutations at positions corresponding thereto.

The mutant may contain three amino acid mutations K511A, I707L, and E708K or mutations at positions corresponding thereto.

The present invention is directed to a method for performing a real-time polymerase change reaction to enhance the discrimination of an allelic or genetic mutation by using the DNA polymerase mutant.

The present invention is directed to a polymerase chain reaction kit containing the DNA polymerase mutant.

MODE FOR CARRYING OUT THE INVENTION

Hereinafter, the present invention will be described in detail with reference to test examples and examples. However, it would be obvious to a person skilled in the art to which the present invention pertains that the scope of the present invention is not limited to the description of test examples and examples below.

<Experimental Example 1> Site Directed Mutagenesis and Construction of Taq DNA Polymerase Mutants The vector pJR-Taq constructed such that the Taq DNA polymerase gene was located downstream of the lac promoter in plasmid pUC18 was used for protein expression. Each mutant was constructed by site-directed mutagenesis along the vector pJR-Taq as a template. Through site-directed mutagenesis of amino acids for mutation by using primers (SEQ ID NOS: 8-93) as follows, corresponding Taq DNA polymerase mutants were constructed. After PCR was performed using Pfu DNA polymerase (Enzynomics, Korea), non-mutated template DNA was removed by treatment with the restriction enzyme DpnI (Enzynomics, Korea), and the mutated plasmids were transformed into *E. coli* DH5α to obtain mutant plasmids. Nucleotide sequence mutations of target sequence sites of the obtained plasmids were sequenced. To minimize the sequence mutations of other sites than the Taq DNA polymerase gene in the vector, each of the obtained mutant plasmids was digested with KpnI/BamHI to give fragments of about 1.3 kb, and pJR-Taq was digested with KpnI/BamHI, ligated to fragments of 3.8 kb from which the fragment of 1.3 kb was removed, and transformed into *E. coli* DH5α, thereby constructing each vector for mutant expression.

TABLE 1

| Site | Variant | Oligo Name | Sequence(5'→3') | Seq. No. |
|---|---|---|---|---|
| G499 | G499R | G499R-F | tttgacgagctaagacttcccgccatcggc | 8 |
| | | G499R-R | gccgatggcgggaagtcttagctcgtcaaa | 9 |
| K505 | K505A | K505A-F | cccgccatcggcgctacggagaagaccggc | 10 |
| | | K505A-R | gccggtcttctccgtagcgccgatggcggg | 11 |
| | K505E | K505E-F | cccgccatcggcgaaacggagaagaccggc | 12 |
| | | K505E-R | gccggtcttctccgtttcgccgatggcggg | 13 |
| | K505S | K505S-F | cccgccatcggctctacggagaagaccggc | 14 |
| | | K505S-R | gccggtcttctccgtagagccgatggcggg | 15 |
| | K505G | K505G-F | cccgccatcggcggtacggagaagaccggc | 16 |
| | | K505G-R | gccggtcttctccgtaccgccgatggcggg | 17 |
| | K505R | K505R-F | cccgccatcggcagaacggagaagaccggc | 18 |
| | | K505R-R | gccggtcttctccgttctgccgatggcggg | 19 |
| | K505F | K505F-F | cccgccatcggcttcacggagaagaccggc | 20 |
| | | K505F-R | gccggtcttctccgtgaagccgatggcggg | 21 |
| | K505I | K505I-F | cccgccatcggcattacggagaagaccggc | 22 |
| | | K505I-R | gccggtcttctccgtaatgccgatggcggg | 23 |
| | K505L | K505L-F | cccgccatcggccttacggagaagaccggc | 24 |
| | | K505L-R | gccggtcttctccgtaaggccgatggcggg | 25 |
| | K505M | K505M-F | cccgccatcggcatgacggagaagaccggc | 26 |
| | | K505M-R | gccggtcttctccgtcatgccgatggcggg | 27 |
| | K505W | K505W-F | cccgccatcggctggacggagaagaccggc | 28 |
| | | K505W-R | gccggtcttctccgtccagccgatggcggg | 29 |
| E507 | E507A | E507A-F | atcggcaagacggctaagaccggcaagcgc | 30 |
| | | E507A-R | gcgcttgccggtcttagccgtcttgccgat | 31 |
| | E507K | E507K-F | atcggcaagacgaagaagaccggcaagcgc | 32 |
| | | E507K-R | gcgcttgccggtcttcttcgtcttgccgat | 33 |
| | E507S | E507S-F | atcggcaagacgtctaagaccggcaagcgc | 34 |
| | | E507S-R | gcgcttgccggtcttagacgtcttgccgat | 35 |
| | E507G | E507G-F | atcggcaagacgggtaagaccggcaagcgc | 36 |
| | | E507G-R | gegcttgccggtcttacccgtcttgccgat | 37 |
| | E507Q | E507Q-F | atcggcaagacgcagaagaccggcaagcgc | 38 |
| | | E507Q-R | gcgcttgccggtcttctgcgtcttgccgat | 39 |
| K511 | K511A | K511A-F | gagaagaccggcgctcgctccaccagcgcc | 40 |
| | | K511A-R | ggcgctggtggagcgagcgccggtcttctc | 41 |
| | K511R | K511R-F | gagaagaccggcagacgctccaccagcgcc | 42 |
| | | K511R-R | ggcgctggtggagcgtctgccggtcttctc | 43 |

TABLE 1-continued

| Site | Variant | Oligo Name | Sequence(5'→3') | Seq. No. |
|---|---|---|---|---|
| | K511E | K511E-F | gagaagaccggcgaacgctccaccagcgcc | 44 |
| | | K511E-R | ggcgctggtggagcgttcgccggtcttctc | 45 |
| | K511S | K511S-F | gagaagaccggctctcgctccaccagcgcc | 46 |
| | | K511S-R | ggcgctggtggagcgagagccggtcttctc | 47 |
| | K511G | K511G-F | gagaagaccggcggtcgctccaccagcgcc | 48 |
| | | K511G-R | ggcgctggtggagcgaccgccggtcttctc | 49 |
| | K511V | K511V-F | gagaagaccggcgttcgctccaccagcgcc | 50 |
| | | K511V-R | ggcgctggtggagcgaacgccggtcttctc | 51 |
| | K511I | K511I-F | gagaagaccggcattcgctccaccagcgcc | 52 |
| | | K511I-R | ggcgctggtggagcgaatgccggtcttctc | 53 |
| | K511L | K511L-F | gagaagaccggccttcgctccaccagcgcc | 54 |
| | | K511L-R | ggcgctggtggagcgaaggccggtcttctc | 55 |
| | K511M | K511M-F | gagaagaccggcatgcgctccaccagcgcc | 56 |
| | | K511M-R | ggcgctggtggagcgcatgccggtcttctc | 57 |
| | K511F | K511F-F | gagaagaccggcttccgctccaccagcgcc | 58 |
| | | K511F-R | ggcgctggtggagcggaagccggtcttctc | 59 |
| | K511Y | K511Y-F | gagaagaccggctatcgctccaccagcgcc | 60 |
| | | K511Y-R | ggcgctggtggagcgatagccggtcttctc | 61 |
| | K511W | K511W-F | gagaagaccggctggcgctccaccagcgcc | 62 |
| | | K511W-R | ggcgctggtggagcgccagccggtcttctc | 63 |
| R512 | R512A | R512A-F | aagaccggcaaggcctccaccagcgccgcc | 64 |
| | | R512A-R | ggcggcgctggtggaggccttgccggtctt | 65 |
| | R512E | R512E-F | aagaccggcaaggaatccaccagcgccgcc | 66 |
| | | R512E-R | ggcggcgctggtggattccttgccggtctt | 67 |
| | R512S | R512S-F | aagaccggcaagtcttccaccagcgccgcc | 68 |
| | | R512S-R | ggcggcgctggtggaagacttgccggtctt | 69 |
| | R512G | R512G-F | aagaccggcaagggttccaccagcgccgcc | 70 |
| | | R512G-R | ggcggcgctggtggaacccttgccggtctt | 71 |
| | R512K | R512K-F | aagaccggcaagaagtccaccagcgccgcc | 72 |
| | | R512K-R | ggcggcgctggtggacttcttgccggtctt | 73 |
| | R512F | R512F-F | aagaccggcaagttctccaccagcgccgcc | 74 |
| | | R512F-R | ggcggcgctggtggagaacttgccggtctt | 75 |
| | R512I | R512I-F | aagaccggcaagatttccaccagcgccgcc | 76 |
| | | R512I-R | ggcggcgctggtggaaatcttgccggtctt | 77 |
| | R512L | R512L-F | aagaccggcaagctttccaccagcgccgcc | 78 |
| | | R512L-R | ggcggcgctggtggaaagcttgccggtctt | 79 |
| | R512M | R512M-F | aagaccggcaagatgtccaccagcgccgcc | 80 |
| | | R512M-R | ggcggcgctggtggacatcttgccggtctt | 81 |

TABLE 1-continued

| Site | Variant | Oligo Name | Sequence(5'→3') | Seq. No. |
|---|---|---|---|---|
| | R512V | R512V-F | aagaccggcaaggtttccaccagcgccgcc | 82 |
| | | R512V-R | ggcggcgctggtggaaaccttgccggtctt | 83 |
| | R512W | R512W-F | aagaccggcaagtggtccaccagcgccgcc | 84 |
| | | R512W-R | ggcggcgctggtggaccacttgccggtctt | 85 |
| | R512Y | R512Y-F | aagaccggcaagtattccaccagcgccgcc | 86 |
| | | R512Y-R | ggcggcgctggtggaatacttgccggtctt | 87 |
| | R512H | R512H-F | aagaccggcaagcactccaccagcgccgcc | 88 |
| | | R512H-R | ggcggcgctggtggagtgcttgccggtctt | 89 |
| I707 | I707L | I707L-F | gtgcgggcctggcttgagaagaccctggag | 90 |
| | | I707L-R | ctccagggtcttctcaagccaggcccgcac | 91 |
| E708 | E708K | E708K-F | cgggcctggattaagaagaccctggaggag | 92 |
| | | E708K-R | ctcctccagggtcttcttaatccaggcccg | 93 |

<Experimental Example 2> Culture for Taq DNA Polymerase Expression

The vectors for Taq DNA polymerase expression were used by introduction into *E. coli* MV1184 (ompT$^+$) or *E. coli* DH5α (DE3) (ompT$^-$). For Taq DNA polymerase expression, *E. coli* was pre-cultured in the LB (1% tryptone, 0.5% yeast extract, 1% NaCl) medium at 37° C. for 8 h, and 1% of the pre-culture broth was seeded in the 2× YT medium (1.6% tryptone, 1.0% yeast extract, 0.5% NaCl) and then main-cultured at 37° C. When the O.D. 600 value of the culture broth reached 0.4-0.6, 0.5 mM IPTG was added and cultured for about 4 h. Upon completion of culture, the culture broth was cooled in iced water and then centrifuged (10,000×g, 10 min, 4° C.) to collect cells. The collected cells were suspended in buffer A [50 mM Tris-Cl (pH 8.0), 1 mM EDTA, 1 μM PMSF (phenylmethylsulfonyl fluoride)] of 1/10 (v/v) of the culture broth, centrifuged, and then collected, and this procedure was repeated twice to remove medium components, and thereafter, the resultant cells were prepared by re-suspension in buffer A of 1/20-1/40 (v/v) of the culture broth.

<Experimental Example 3> Preparation of Crudely Purified Taq DNA Polymerase Sample Taq DNA polymerase was crudely purified from the cell suspension obtained from 100 ml of the culture broth (Experimental Example 2). The cell suspension was homogenized using an ultrasonic homogenizer (2 mm tip, amplitude 25%, 9.9 s/3 s (on/off), 5 min) to disrupt the cells, and then centrifuged (10,000×g, 10 min, 4° C.) to obtain a supernatant. RNase was added to the supernatant to 50 μg/ml, followed by incubation at 37° C. for 30 min, and then the resultant product was heat-treated at 75° C. for 20 min and centrifuged (10000×g, 10 min, 4° C.) to collect a supernatant (4.0 ml), thereby obtaining a crudely purified sample. This sample was used for Taq DNA polymerase activity comparison experiments after protein quantification.

<Experimental Example 4> High-Purity Purification of Taq DNA Polymerase

Taq DNA polymerase was purified with high purity from the cell suspension obtained from 4.5 L of the culture broth. The cells of the cell suspension (100 ml) were disrupted using an ultrasonic homogenizer (13 mm tip, amplitude 90%, 5.5 s/9.9 s (on/off), 1 h), and then centrifuged (10,000×g, 10 min, 4° C.) to obtain a supernatant. Streptomycin sulfate was added thereto to 5%, stirred for 30 min, and then centrifuged (10,000×g, 10 min, 4° C.) to collect a supernatant. This liquid was heat-treated at 75° C. for 20 min, and the sample was again centrifuged (10,000×g, 10 min, 4° C.), and the supernatant thus obtained was filtered through a 0.45-μm syringe filter (Sartorius). Ammonium sulfate was added to the filtrate to reach a saturation of 65% for Taq DNA polymerase protein precipitation, and after 1 hour at 4° C., the precipitate was collected by centrifugation (10,000×g, 10 min, 4° C.) and suspended in 10 ml of buffer A. The suspension was placed in a dialysis membrane (Spectra/Por, MWCO: 12-14 KDa) and dialyzed in 4 L of buffer A overnight to remove salts. The desalted solution was filtered through a 0.45-μm syringe filter (Sartorius) and purified by FPLC (AKTA, UPC-900). Column chromatography was performed in the order of DEAE Sephacel (30 ml in XK26/20 column, GE healthcare), SP sepharose (20 ml in XK16/20 column, GE healthcare), and heparin sepharose (10 ml in HR16 column, GE healthcare). For column equilibration, buffer A (DEAE Sephacel and heparin sepharose columns) and buffer B [20 mM HEPES (pH 6.9), 1 mM EDTA, 1 uM PMSF](Q sepharose column) were used, and as for elution, proteins were eluted with a concentration gradient by using buffer A and buffer B containing 1 M KCl. Elution fractions containing Taq DNA polymerase were collected in each column step and filtered with VIVASPIN20 (MW: 50,000). This filtering was performed for salting or washing and concentration for activity tests, and the fractions collected from each column were concentrated over VIVASPIN20 (MW: 50,000), and then washed and filtered with about 15 ml of buffer A or B in the next step twice repeatedly.

For a column in the next step, the resultant product was dissolved in 10-20 ml of the same buffer and then applied to the column, or dissolved in an appropriate solution depending on the test.

The Taq DNA polymerase obtained in each purification step or by final purification was quantified and compared using SDS-PAGE (12% polyacryl amide gel electrophoresis) and Bradford assay reagent (Sigma), along with bovine serum albumin as a standard protein.

The crudely purified or purified Taq DNA polymerase was mixed with a storage buffer containing 50 mM Tris-Cl (pH 8.0), 0.5 mM EDTA, 1 μM PMSF, 4 mM KCl, 2 mM $MgCl_2$, 1 mM DTT, and 50% glycerol in final concentrations, and stored at −70° C. before use for tests.

<Experimental Example 5> Comparison of Taq DNA Polymerase Mutant Activity

The activity comparison and measurement between a Taq DNA polymerase mutant and wild-type Taq DNA polymerase were made by performing conventional PCR while the quantified protein amounts were adjusted to be constant, followed by electrophoresis. The lambda phage DNA (10 μg, Bioneer) was used as a template while lambda-F (5'-GTGCTTTTATGACTCTGCCGC) (SEQ ID NO: 105) and lambda-R (5'-AGGCCCTTCCTGGTATGC) (SEQ ID NO: 106) at 10 pmol for each were used as primers, and the reaction at 94° C. (5 min), cycles of 94° C. (30 s)-55° C. (30 s)-72° C. (30 s), and then 72° C. (7 min) in PCR buffer [10 mM Tris-Cl (pH 9.0), 1.5 mM $MgCl_2$, 40 mM KCl, 0.6 M Methyl-α-D-glucopyranoside, 0.03% tween 20, 3 mM dNTP] was conducted and then ended. The DNA amplification product (500 bp) was examined by electrophoresis.

<Experimental Example 6> Real-Time PCR for Examining Determination

Unless otherwise stated in the examples below, compositions and conditions for PCR used in the examples of the present invention are as follows.

As for template DNAs used for PCR, DNAs for the normal (SEQ ID NO: 3) or mutant (SEQ ID NO: 4) sequence of each target detection gene, BRAF c.1799 rc. A>T (p. V600E) (hereinafter BRAF-V600E) and the normal (SEQ ID NO: 5) or mutant (SEQ ID NO: 6) sequence of EGFR c.2369 C>T (p.T790M) (hereinafter BRAF-T790M) were synthesized, inserted into pTOP Blunt V2 (Enzynomics, Korea), and transformed into *E. coli*, and then the cultured and purified plasmid DNAs were digested with restriction enzymes, purified, and then quantified to become $2\times10^7$ copy/reaction.

(BRAF V600 normal (rc))

SEQ ID NO: 3

AAAATATTCGTTTTAAGGGTAAAGAAAAAAGTTAAAAAATCTATTTACAT

AAAAAATAAGAACACTGATTTTTGTGAATACTGGGAACTATGAAAATACT

ATAGTTGAGACCTTCAATGACTTTCTAGTAACTCAGCAGCATCTCAGGGC

CAAAAATTTAATCAGTGGAAAAATAGCCTCAATTCTTACCATCCACAAAA

TGGATCCAGACAACTGTTCAAACTGATGGGACCCACTCCATCGAGATTTC

ACTGTAGCTAGACCAAAATCACCTATTTTTACTGTGAGGTCTTCATGAAG

AAATATATCTGAGGTGTAGTAAGTAAAGGAAAACAGTAGATCTCATTTTC

-continued

CTATCAGAGCAAGCATTATGAAGAGTTTAGGTAAGAGATCTAATTTCTAT

AATTCTGTAATATAATATTCTTTAAAACATAGTACTTCATCTTTCCTCTT

AGAGTCAATAAGTATGTCTAAAACAATGATTAGTTCTATTTAGCCTATAT

A (BRAF V600E mutant (rc))

SEQ ID NO: 4

AAAATATTCGTTTTAAGGGTAAAGAAAAAAGTTAAAAAATCTATTTACAT

AAAAAATAAGAACACTGATTTTTGTGAATACTGGGAACTATGAAAATACT

ATAGTTGAGACCTTCAATGACTTTCTAGTAACTCAGCAGCATCTCAGGGC

CAAAAATTTAATCAGTGGAAAAATAGCCTCAATTCTTACCATCCACAAAA

TGGATCCAGACAACTGTTCAAACTGATGGGACCCACTCCATCGAGATTTC

TCTGTAGCTAGACCAAAATCACCTATTTTTACTGTGAGGTCTTCATGAAG

AAATATATCTGAGGTGTAGTAAGTAAAGGAAAACAGTAGATCTCATTTTC

CTATCAGAGCAAGCATTATGAAGAGTTTAGGTAAGAGATCTAATTTCTAT

AATTCTGTAATATAATATTCTTTAAAACATAGTACTTCATCTTTCCTCTT

AGAGTCAATAAGTATGTCTAAAACAATGATTAGTTCTATTTAGCCTATAT

A (BRAF T790 normal)

SEQ ID NO: 5

CACGCACACACATATCCCCATGGCAAACTCTTGCTATCCCAGGAGCGCAG

ACCGCATGTGAGGATCCTGGCTCCTTATCTCCCCTCCCCGTATCTCCCTT

CCCTGATTACCTTTGCGATCTGCACACACCAGTTGAGCAGGTACTGGGAG

CCAATATTGTCTTTGTGTTCCCGGACATAGTCCAGGAGGCAGCCGAAGGG

CATGAGCTGCGTGATGAGCTGCACGGTGGAGGTGAGGCAGATGCCCAGCA

GGCGGCACACGTGGGGGTTGTCCACGCTGGCCATCACGTAGGCTTCCTGG

AGGGAGGGAGAGGCACGTCAGTGTGGCTTCGCATGGTGGCCAGAAGGAGG

GGCACATGGACCCCTTCCAGGTGAAGACGCATGAATGCGATCTTGAGTTT

CAAAATACGTACTCATGGAGGAAAAGCTGTGCCTGCAAAAGACCTAGC (BRAF T790M mutant)

SEQ ID NO: 6

CACGCACACACATATCCCCATGGCAAACTCTTGCTATCCCAGGAGCGCAG

ACCGCATGTGAGGATCCTGGCTCCTTATCTCCCCTCCCCGTATCTCCCTT

CCCTGATTACCTTTGCGATCTGCACACACCAGTTGAGCAGGTACTGGGAG

CCAATATTGTCTTTGTGTTCCCGGACATAGTCCAGGAGGCAGCCGAAGGG

CATGAGCTGCATGATGAGCTGCACGGTGGAGGTGAGGCAGATGCCCAGCA

GGCGGCACACGTGGGGGTTGTCCACGCTGGCCATCACGTAGGCTTCCTGG

AGGGAGGGAGAGGCACGTCAGTGTGGCTTCGCATGGTGGCCAGAAGGAGG

GGCACATGGACCCCTTCCAGGTGAAGACGCATGAATGCGATCTTGAGTTT

CAAAATACGTACTCATGGAGGAAAAGCTGTGCCTGCAAAAGACCTAGC

The forward primer 5-GGGACCCACTCCATCGAGATTTCT-3'-(BRAF-AS-F; SEQ ID NO: 94); the reverse primer 5'-AACTCTTCATAATGCTTGCTCTGATAG-3'-(BRAF-R; SEQ ID NO: 95); and the signal probe 5-FAM-CTGTGAGGTCTTCATGAAG-BHQ1-3'-(BRAF-P; SEQ ID NO: 96) were used to examine the discrimination of BRAF-V600E mutation, and the forward primer 5'-AGCCGAAGGGCATGAGCTGCA-3'-(EGFR-AS-F;

SEQ ID NO: 97) or 5'-AGCCGAAGGGCATGAGCTACA-3'-(EGFR-ARMS-F; SEQ ID NO: 98); the reverse primer 5-AGTGTGGACAACCCCCACGTGTGC-3'-(EGFR-R; SEQ ID NO: 99); and the signal probe 5-FAM-CGGTG-GAGGTGAGGCAGATG-BHQ1-3'-(EGFR-P; SEQ ID NO: 100) were used to examine the discrimination of EGFR-T790M mutation. In particular, the forward primers are AS primers or ARMS primers that are designed such that for the detection of mutations in the respective target detection genes BRAF-T790M and BRAF-V600E, the final 3'-terminal base is matched with mutant genes or the final terminal base is mismatched with normal genes. Each primer was used at 10 pmol/reaction, and the probe was used at 20 pmol/reaction.

PCR for discrimination of BRAF-V600E was performed at 95° C. (5 min) and then 50 cycles of 95° C. (30 s)-55° C. (1 minute), and PCR for discrimination for EGFR-T790M was performed at 95° C. (5 min) and then 50 cycles of 95° C. (30 sec)-55° C. (40 s).

A buffer for PCR contained 10 mM Tris, pH 9.0, 1.5 mM $MgCl_2$, 1 mM dNTPs, 60 mM KCl, and 10 mM $((NH_4)_2SO_4)$, and PCR was performed using a CFX96 real-time PCR detection system (Bio-Rad, Hercules, CA, USA). However, for respective examples, the concentration of KCl may be changed; betaine or the like may be added; the type of enzyme (depending on the wild type or Tag DNA polymerase mutant) or the amount of the enzyme may be changed. The discrimination between matches and mismatches of the invented DNA polymerase mutants was evaluated as ΔCt (ΔCt=Ct value of variant template−Ct value of wild-type template).

<Example 1> Taq DNA Polymerase Degradation According to Expressing Parent Strain *E. coli*

Figure 2A:
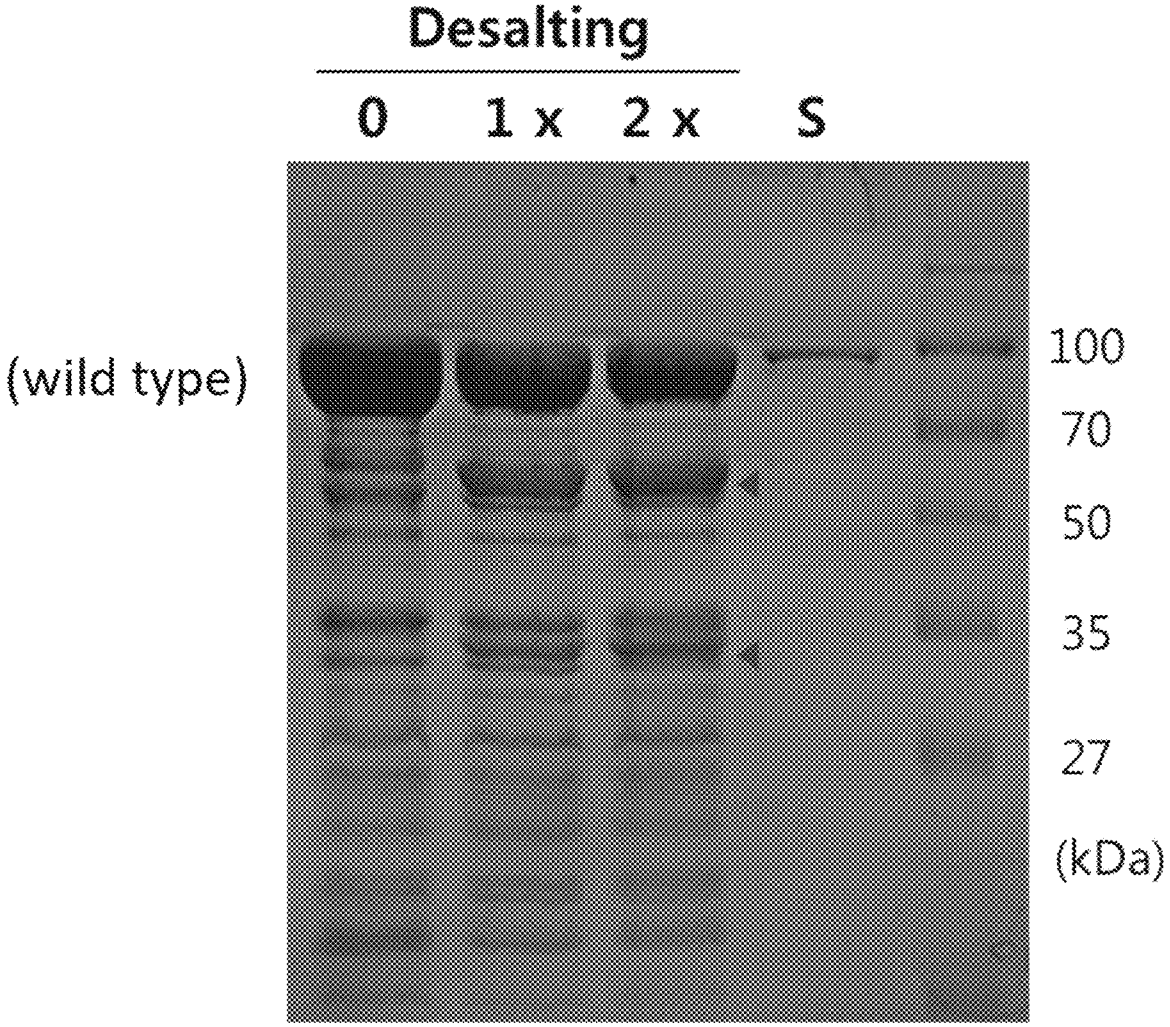
FIGS. 2A-2C illustrates SDS-PAGE images of Taq DNA polymerase.
Figure 2B:
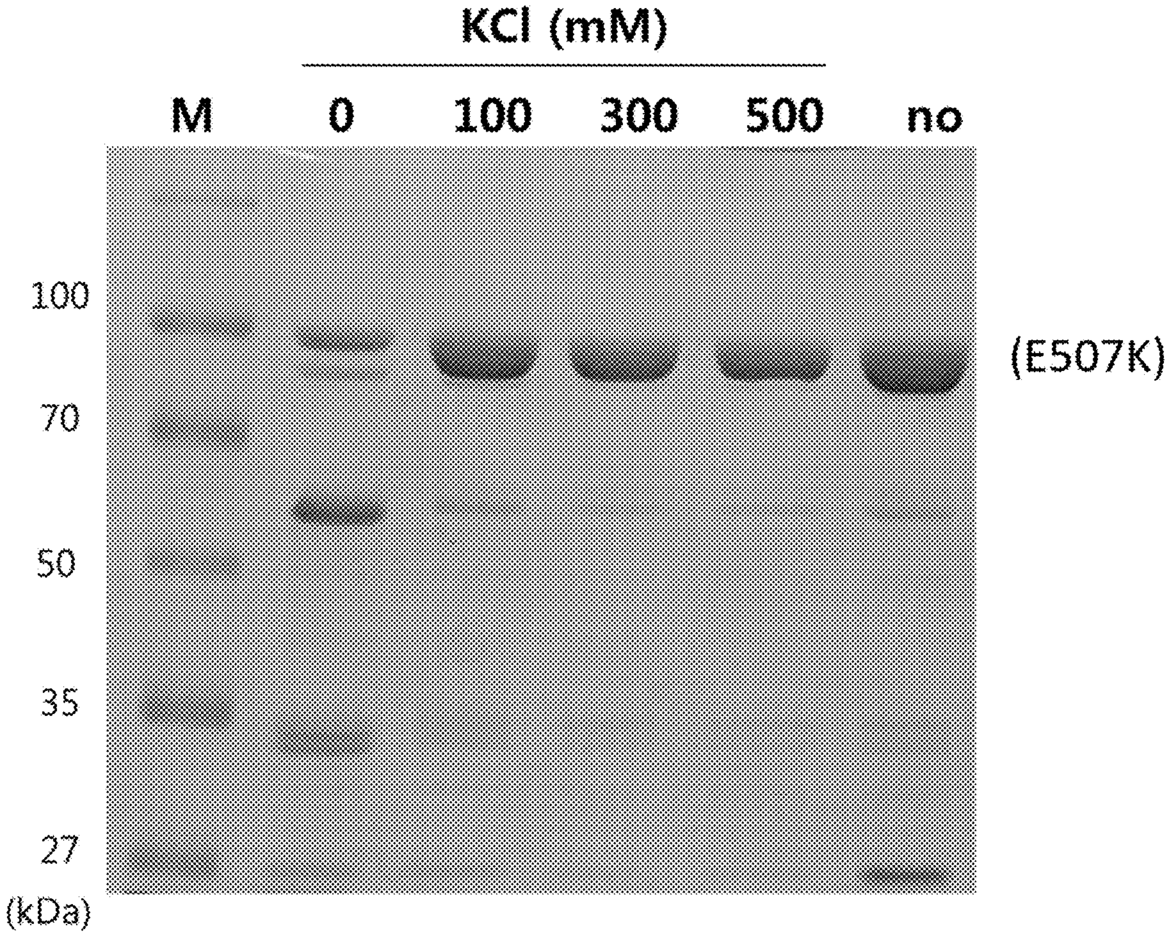
Figure 2C:
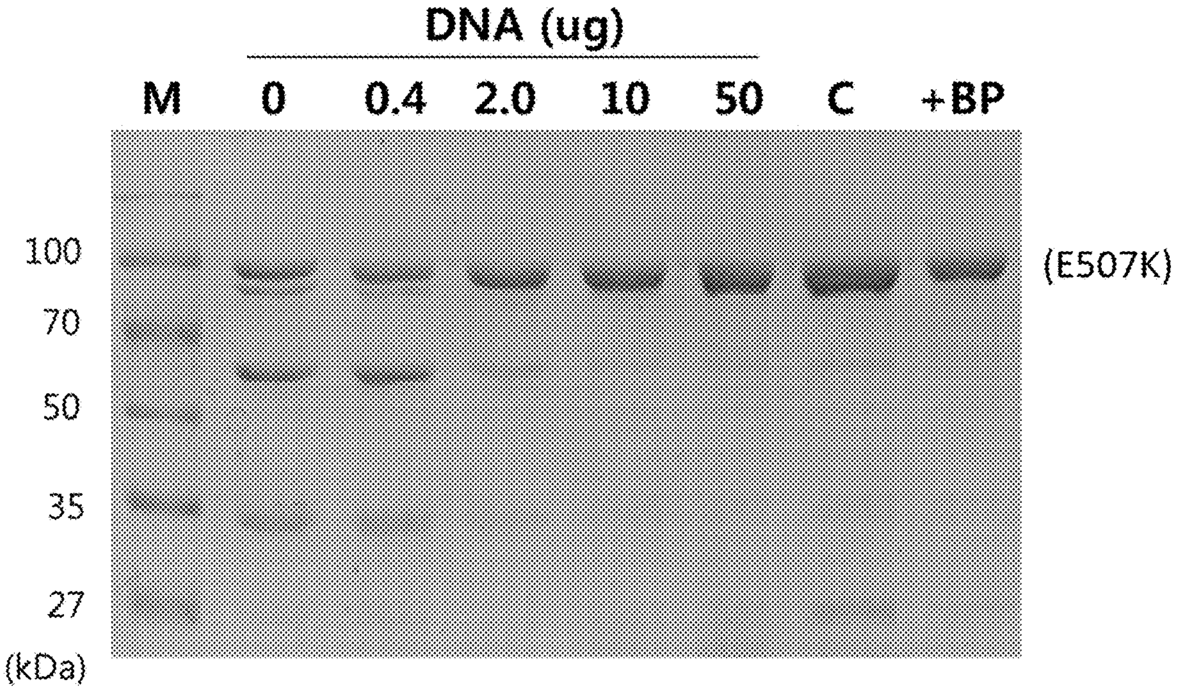

As for the Taq DNA polymerase cultured and expressed as in <Experimental Example 2>, the Taq polymerase fractions were subjected to filtration with VIVASPIN20 (MW: 50,000) using buffer A in the DEAE column chromatography purification step as in <Experimental Example 4>. Proteins were investigated by SDS-PAGE. During this procedure, the Taq DNA polymerase expressed in *E. coli* BL21(DE3) ($ompT^-$) as an OmpT mutant strain was not degraded, but the wild-type Taq DNA polymerase (SEQ ID NO: 1) expressed in *E. coli* MV1184 ($ompT^+$), which was not an OmpT mutant strain, was partially degraded during purification (FIG. 2A). When the same procedure was performed, more degradation occurred during the purification of, especially, the Taq DNA polymerase containing E507K mutation expressed in *E. coli* MV1184 (omp T) (FIG. 2B). That is, the degradation of Taq DNA polymerase during purification showed distinctively different patterns according to the expressing parent strain, and more apparent degradations occurred in the Taq DNA polymerase containing E507K mutation.

<Example 2> Inhibition of Taq DNA Polymerase Degradation by High-Concentration KCl This degradation occurred rapidly in the washing in which the Taq DNA polymerase obtained by DEAE column chromatography was filtered with VIVASPIN20 (MW: 50,000) using buffer A, during the purification process in <Experimental Example 4>.

The fractions in the DEAE Sephacel chromatography purification step of the Taq DNA polymerase mutant containing E507K mutation cultured and purified as in <Experimental Example 2> or <Experimental Example 4> were obtained. Then, 50 μl (about 4 μg of protein/pl) of the fraction samples were filtered with VIVASPIN20 (MW: 50,000, 50 ml volume) using only buffer A without KCl (0 M KCl) and buffer A containing 100, 300, or 500 mM KCl in two categories, and then dissolved in buffer A containing the same concentrations of KCl as in the respective filtration test groups. The dissolved Taq DNA polymerases for the respective test groups were subjected to SDS-PAGE, and as a result, as for 0 mM KCl, protein fragments of about 33 KDa and about 60 KDa were newly observed due to degradation and the amount of the original DNA polymerase was significantly reduced. However, the filtration using buffer A containing KCl at 100 mM or more showed no difference compared with the non-treatment group. It could be therefore seen that the Taq DNA polymerase degradation was inhibited by high-concentration KCl (FIG. 2B).

<Example 3> Inhibition of Taq DNA Polymerase Degradation by DNA

The fractions through the DEAE Sephacel chromatography purification step of the Taq DNA polymerase containing E507K mutation were obtained as in <Experimental Example 2> or <Experimental Example 4>. Then, 50 μl of the fraction samples (about 4 μg of protein/pl) were mixed with a double volume (100 pl) of fractions (BP), obtained after the Taq DNA polymerase was eluted on DEAE column chromatography, and then filtering was conducted as in <Experimental Example 4>. The filtering process with VIVASPIN20 (MW: 50,000) was conducted using buffer A, and the samples collected by dissolution in 250 μl of buffer A were subjected to SDS-PAGE to examine protein degradation. As a result, surprisingly, the degradation of Taq DNA polymerase occurred in the samples not mixed with BP, but the degradation did not occur in the sample mixed with BP. As a result of Bradford measurement and SDS-PAGE analysis of the used BP, the BP contained few proteins but contained a large amount of nucleic acids (~50 ng/μl). It was therefore presumed that a degradation inhibitor is a nucleic acid, such as DNA, rather than an unknown protein.

In accordance with the above results, 50 μl of the fractions through the DEAE Sephacel chromatography purification step of the Taq DNA polymerase mutant containing E507K mutation were mixed with 0.4, 2.0, 10, or 50 μg of DNA (salmon sperm nucleic acid, Sigma) to prepare samples, which were then subjected to the same filtration process using buffer A. As a result, Taq DNA polymerase was not degraded in the test groups treated with DNA at 2.0 μg or more as in the BP treatment group. This clearly showed that the nucleic acid inhibited the degradation of Taq DNA polymerase by a protease. That is, these results indicated that the degradation site of Taq DNA polymerase was associated with an important site for binding with DNA or a site binding with DNA.

<Example 4> Determination of Cleavage Site of Taq DNA Polymerase

The sample (purity of 96% or higher) obtained in the DEAE column chromatography purification step of a Taq DNA polymerase mutant containing E507K mutation cultured and purified as in <Experimental Example 2> or <Experimental Example 4> was filtered and washed with buffer A as in <Experimental Example 4>, and collected using buffer A, and then subjected to complete degradation at up to 10° C. (FIG. 3). As a result of investigating the degraded products by SDA-PAGE, the large fragment was about 60 KDa in size and the small fragment was about 33 KDa in size.

The SDS-PAGE gel on which the two fragments were electrophoresed was cut to collect protein fragments, which were then subjected to amino acid sequencing. As a result, the 60 KDa fragment was identified as an N-terminal fragment of Taq polymerase and the 33 KDa fragment was identified as a C-terminal fragment thereof. Based on these results, the N-terminal sequence of 33 KDa was analyzed to investigate a more accurate cleavage site. The results confirmed that the N-terminal sequence of the 33 KDa fragment was R-S-T-S . . . . The sequence corresponding thereto on the Taq DNA polymerase was R512-S513-T514-S515, and thus the cleavage site was determined between K511 and R512 (FIG. 4).

Interestingly, K511 and R512 corresponding to the cleavage site consist of two consecutive positively charged amino acids. These consecutive positively charged amino acids are well known as a cleavage site preferred by the membrane protease OmpT of *E. coli*. It has been reported that the presence of negatively charged amino acids within several amino acid residues (P6 to P'6) at both sides of a cleavage site by OmpT significantly inhibited the protein cleavage by OmpT (Hritonenko and Stathopoulos 2007, Schechter and Berger 2012).

According to Examples 1 to 3, the Taq DNA polymerase mutant containing E507K mutation was more degraded than the wild-type Taq DNA polymerase, and the reason seems to be that E507 corresponding to the P5 position of the OmpT recognition site was changed from the negatively charged amino acid glutamic acid (glu, E) to the positively charged amino acid lysine (lys, K). That is, it was explained that the E507K mutation Taq DNA polymerase had a greater substrate affinity for OmpT than the wild-type Taq DNA polymerase, so that the peptide bond between K511 and R512 [P1(K)-P1'(R)], which are adjacent consecutive positively charged amino acid residues, was easily cleaved by OmpT protease (FIG. 4).

The inhibition of the DNA polymerase degradation at a high concentration of KCl in <Example 2> was presumed to be inhibiting the degradation activity of OmpT protease by KCl.

In addition, the degradation of DNA polymerase was inhibited by DNA in <Example 3> (FIG. 3), and it can be therefore seen that the DNA polymerase site interacting with or cleaved by OmpT protease binds to DNA. Hence, it can be obviously seen that the Taq DNA polymerase cleavage site (511 and 512) and adjacent sites thereof are a region corresponding to DNA.

<Example 5> Structure and Cleavage Site of Taq DNA Polymerase

The K511-R512 site, where degradation occurred, confirmed in <Example 4>, is present in the loop region (497-514) between Ha (487-496) and Hb (515-521) with small α-helical structures, corresponding to the tip of the thumb domain of Taq DNA polymerase (FIGS. 1 and 5).

Ha and Hb are conserved regions with high homology between family A DNA polymerases, but the loop region consists of a relatively less conserved region. Very interestingly, this region is characterized by containing few negatively charged amino acids and a large number of positively charged amino acids.

The loop structure between Ha (487-496) and Hb (515-521) in the thumb domain of Taq DNA polymerase was predicted to be present near a primer region (Kim, Eom et al. 1995), but the importance of this region was not noticed prior to the present invention. The reason was that this region showed a highly disordered state in the formation of a crystal structure, and thus the structural relationship thereof with substrates including primers could not be clearly identified.

The structure of the loop region was thoroughly checked through PyMOL (pymol.org) software by using 3KTQ information as crystal structure DB for binding between Taq DNA polymerase and DNA in protein database (PDB, rcsb.org). As a result, it was confirmed that this loop structure surrounds the backbone region of the primer (FIG. 5). This structure shows the relevance of the inhibition of the Taq DNA polymerase degradation by DNA.

It could be confirmed from these structural characteristics and Taq DNA polymerase degradation characteristics that this loop region is closely associated with the binding to DNA including primers.

The loop region of Taq DNA polymerase interacting with the primer can be a very important site for the development of an enzyme mutant that improves PCR efficiency or discrimination. The amino acids of the loop region may be an important engineering target region, and especially, the charged amino acids present in this region may be selected as a target of primary engineering. Since the positively charged amino acids of the loop region are capable of electrostatic interaction with negative charges of the phosphate backbone of the primer, the mutations thereof can be expected to change the activity of Taq DNA polymerase, especially, to change the characteristics of the polymerases exhibiting discrimination.

<Example 6> Construction and Activity Verification of K511A Mutant and R512A Mutant It was attempted to determine whether discrimination-related mutant strains corresponding to the purpose of the present invention could be selected by engineering the positively charged amino acids K511 and R512, which were a preferred cleavage region, among several amino acids present in the loop region, according to the reasoning of <Example 5>. K511A and R512A Taq DNA polymerase mutants were constructed by changing K511 and R512 to alanine (A), which is a representative uncharged amino acid, by site-directed mutagenesis in <Experimental Example 1>. These mutants were expressed in *E. coli* BL21 (DE3), and each Taq DNA polymerase mutant were crudely purified and measured for activity through PCR, and as a result, the K511A mutant had high activity comparable to that of wild-type Taq DNA polymerase, but the R512A mutant showed no Taq DNA polymerase activity. It was assumed from the above results that the positively charged amino acid arginine at the position of R512 rather than K511 would play a very important role in the binding with a primer.

<Example 7> Discrimination Between Match and Mismatch in K511A Mutant

The K511A Taq DNA polymerase mutant constructed in <Example 6> was cultured as in <Experimental Example 2> and <Experimental Example 4>, and purified to a purity of 95% or more by SDS-PAGE. The purified K511A Taq DNA polymerase was subjected to real-time PCR as in <Experimental Example 6>. In the conditions of PCR that has been performed, the K511A Taq DNA polymerase showed significantly higher discrimination compared with wild-type Taq DNA polymerase. The 3'-mismatch discrimination by the K511A mutant was determined on BRAF-V600E [A and T base discrimination (template DNAs; SEQ ID NOs: 5 and 6)] and EGFR-T790M [C and T base discrimination (template DNAs; SEQ ID NOs: 3 and 4)]. As a result, high discrimination between a match and a mismatch was shown in real-time PCR using the K511A Taq DNA polymerase (FIG. 6).

<Example 8> Effects of KCl and Betaine in PCR Using K511A Taq

When KCl with a gradually increasing concentration of 0 to 180 nM was added to the K511A Taq DNA polymerase mutant purified as in <Example 7>, the activity changes of the K511A mutant were compared with those of wild-type Taq DNA polymerase (Table 3). The wild-type Taq DNA polymerase retained relatively high activity even at a high KCl concentration, and as the enzyme concentration increased, the discrimination between matches and mismatches tended to increase. Especially, the K511A mutant retained activity up to a KCl concentration of about 80 mM in BRAF-V600E detection and up to a KCl concentration of about 100 mM in EGFR-T790M detection, and in both of the cases, the higher the concentration of the enzyme mutant, the higher the discrimination, while the lower the concentration of the enzyme mutant, the lower the discrimination. Under the addition of betaine (1.25 M), the activity of the K511A mutant was somewhat stronger, and the concentration range of KCl was further extended, so that the mutant showed high activity at a KCl concentration of about 100 mM or more in BRAF-V600E detection and even at a KCl concentration of about 120 mM or move in EGFR-T790M detection.

Considering the results of the example, appropriate concentration ranges of KCl and betaine for optimal PCR discrimination between matches and mismatches by using the K511A mutant may vary depending on the target template and primer or PCR conditions.

TABLE 2

| BRAF (V600E) | DNA Polymerase | Ct value | No betaine | | | Add betaine (1.25M) | | |
|---|---|---|---|---|---|---|---|---|
| BRAF (V600E) | DNA Polymerase | Ct value | KCl (mM) | | | KCl (mM) | | |
| BRAF (V600E) | DNA Polymerase | Ct value | 60 | 80 | 100 | 60 | 80 | 100 |
| BRAF (V600E) | wild-type Taq DNA polymerase | Ct of Mt | 18.38 | 18 | 16.3 | 17.7 | 17.56 | 17.04 |
| BRAF (V600E) | wild type Taq DNA polymerase | Ct of Wt | 25.54 | 26.62 | 28.57 | 22.68 | 22.97 | 23.92 |
| BRAF (V600E) | wild type Taq DNA polymerase | ΔCt | 7.16 | 8.62 | 12.27 | 4.98 | 5.41 | 6.88 |
| BRAF (V600E) | K511A Taq DNA polymerase | Ct of Mt | 15.25 | 14.84 | no signal | 16.41 | 15.78 | 16.57 |
| BRAF (V600E) | K511A Taq DNA polymerase | Ct of Wt | 31.52 | 33.36 | no signal | 29.64 | 30.68 | no signal |
| BRAF (V600E) | K511A Taq DNA polymerase | ΔCt | 16.27 | 18.52 | nd | 13.23 | 14.9 | >16.57 |
| EGFR (T790M) | DNA Polymerase | Ct value | KCl (mM) | | | KCl (mM) | | |
| EGFR (T790M) | DNA Polymerase | Ct value | 80 | 100 | 120 | 80 | 100 | 120 |
| EGFR (T790M) | wild-type Taq DNA polymerase | Ct of Mt | 16.91 | 16.14 | 15.82 | 16.98 | 16.66 | 16.98 |
| EGFR (T790M) | wild type Taq DNA polymerase | Ct of Wt | 19.9 | 20.64 | 21.14 | 18.03 | 18.34 | 18.71 |
| EGFR (T790M) | wild type Taq DNA polymerase | ΔCt | 2.99 | 4.5 | 5.32 | 1.05 | 1.68 | 1.73 |
| EGFR (T790M) | K511A Taq DNA polymerase | Ct of Mt | 15.6 | 18.58 | no signal | 16.19 | 16.02 | 16.08 |
| EGFR (T790M) | K511A Taq DNA polymerase | Ct of Wt | 23.96 | 40.08 | no signal | 22.48 | 23.94 | 25.78 |
| EGFR (T790M) | K511A Taq DNA polymerase | ΔCt | 8.36 | 21.5 | nd | 6.29 | 7.92 | 9.7 |
| EGFR (T790M) | | | | | | | | |

In the table above, Mt represents mutant DNA template and Wt represents wild-type DNA template.

<Example 9> Construction Activity of Mutants Having Charged Amino Acids in Loop Region A number of mutants where G499, K505, E507, K508, K511, and R512, charged amino acids in the loop region, were selected and substituted with some types of representative amino acids [A, G, S, K (or R), and E] among 20 amino acids, and tested for activity and mutation discrimination. Each mutant was constructed using each primer set for mutant construction according to <Experimental Example 1>.

The mutants were cultured using *E. coli* BL21(DE3) as a parent strain according to <Experimental Example 2> and crudely purified according to <Experimental Example 3>, and these crudely purified samples were tested for activity according to <Experimental Example 5>. Each of the crudely purified Taq DNA polymerase samples was quantified by Bradford assay, and diluted to, starting approximately 600 ng of proteins, 2× (300 ng), 4× (150 ng), 16× (75 ng), and 32× (37.5 ng), and then evaluated by PCR (Table 3).

As a result, the substitutions of the positively charged amino acids K505, K508, K511, and R512 with the negatively charged amino acid glutamic acid, that is, K505E, K508E, K511E, and R512E mutants showed no DNA polymerase activity. However, the substitutions with the same type of positively charged amino acids still showed very high polymerase activity.

It could be confirmed from such results that the positively charged amino acids lysine (K) and arginine (R) were very important for activity. This loss of polymerase activity is considered to result from the weakening of the binding between the loop region and phosphoric acid of the backbone of DNA including primers due to the change of a positively charged amino acid to a negatively charged amino acid. On the contrary, the mutants obtained by changing glutamic acid (E507), the only negatively charged amino acid in the loop region, to lysine (K) had no decrease in activity or rather increased activity. Furthermore, the substitution of G499, an uncharged amino acid, with arginine (R), a positively charged amino acid, showed high enzyme activity.

TABLE 3

| Polymerase | Dilution rate | | | | | | activity* | Discrimination** |
|---|---|---|---|---|---|---|---|---|
| 중합효소 | 1 | 2 | 4 | 8 | 16 | 32 | 활성* | 구분성** |
| WT | ○ | ○ | ○ | ○ | ○ | ○/X | +++ | |
| K505G | ○ | ○ | X | | | | + | +++ |
| K505I | ○ | ○ | ○ | X | | | +++ | +++ |
| K505L | ○ | ○ | ○ | X | | | +++ | +++ |
| K505M | ○ | ○ | ○ | X | | | +++ | +++ |
| K505W | ○ | X | | | | | + | nd |
| K505F | ○ | ○ | ○ | ○ | X | | +++ | +++ |
| E507A | ○ | ○ | ○ | ○ | ○ | X | +++ | nd |
| E507G | ○ | ○ | ○ | ○ | ○ | X | +++ | + |
| E507S | ○ | ○ | ○ | ○ | ○ | X | +++ | nd |
| E507K | ○ | ○ | ○ | ○ | ○ | ○/X | +++ | – |
| K508A | ○ | ○ | X | | | | + | +++ |
| K508G | ○ | ○ | ○ | X | | | ++ | nd |
| K508S | ○ | ○ | X | | | | ++ | +++ |
| K508R | ○ | ○ | ○ | ○ | ○ | ○/X | +++ | + |
| K511A | ○ | ○ | ○ | X | | | ++ | +++ |
| K511S | ○ | X | | | | | + | nd |
| K511R | ○ | ○ | ○ | ○ | X | | +++ | ++ |
| K511M | ○ | X | | | | | + | nd |

TABLE 3-continued

| Polymerase | Dilution rate | | | | | | activity* | Discrimination** |
|---|---|---|---|---|---|---|---|---|
| 중합효소 | 1 | 2 | 4 | 8 | 16 | 32 | 활성* | 구분성** |
| R512K | ○ | ○ | ○ | ○ | X | | +++ | ++ |
| R512F | ○ | X | | | | | + | nd |
| R512I | ○ | X | | | | | + | nd |
| R512L | ○ | X | | | | | + | nd |
| R512W | ○ | X | | | | | + | +++ |
| R512Y | ○ | X | | | | | + | nd |
| CS2-K511A | ○ | ○ | X | | | | ++ | +++ |

*+++ was marked when active at ⅛ or greater dilution;
++ was marked when active at ½ to less than ⅛ dilution;
+ was marked when active at less than ½ dilution; and
– was marked when no activity was detected in stock solution.
**The discrimination was expressed as ΔΔCt.
ΔΔCt = ΔCt of wild-type (WT) Taq DNA polymerase (ΔCt = Ct of mutant template – Ct of wild-type template) – ΔCt of Taq DNA polymerase mutant.
The test was evaluated by the discrimination of BRAF-V600E mutation.
In the table,
– was marked for ΔΔCt of less than 1;
+ was marked for ΔΔCt of 1 to less than 3;
++ was marked for ΔΔCt of 3 to less than 6; and
+++ was marked for ΔΔCt of 6 or more.
If not detected, it was expressed as nd.

<Example 10> Comparison of Real-Time PCR Discrimination Among DNA Polymerase Mutants Among various Taq DNA polymerase mutants crudely purified as in <Example 8>, Taq DNA polymerase mutant crudely purified samples with activity of ++ or higher were subjected to real-time PCR for examining the discrimination according to Experimental Example 6. The results are shown in the discrimination column on Table 3. The discrimination was evaluated by comparing the values of ΔΔCt (ΔΔCt=ΔCt of wild-type Taq–ΔCt of mutant Taq, and ΔCt=Ct of mutant template–Ct of wild-type template).

Among the test mutants, the mutants with relatively high discrimination (++) were K511R and R512K, and the mutants with very high discrimination (+++) were K505G, K505I, K505L, K505M, K505F, K508S, K508R, K511A, and R512W (Table 3 and FIGS. 7A and 7B).

The activity of the mutants having substitutions with negatively charged amino acids (K505E, K508E, K511E, and R512E) was significantly reduced as shown in Example 9, and similarly, the mutants with the removal of negatively charged amino acids (E507G, E507K, and E507Q) showed comparatively high activity but did not show significantly high discrimination. Interestingly, when the positively charged amino acids K and R were substituted with each other, that is, the K511R and R512K mutants had retained activity and slightly enhanced discrimination. Among the respective mutants, the mutants showing high discrimination were identified to be K505G, K505I, K505L, K505M, K505F, K508S, K511A, and R512W, which were mutants having substitutions with uncharged amino acids.

Considering these results, it is considered that the presence of negatively charged amino acids in the loop region, which is a concentrated mutation region of the present invention, interferes with the binding between phosphoric acid of the DNA backbone and the loop region, thereby causing a reduction in activity, and it is determined that the presence of positively charged amino acids in the loop region induced strong binding between a protein and a primer and thus is advantageous in retaining stable activity. The substitution of a positively charged amino acid with an uncharged amino acid in the loop region leaded to a low loss of activity and high discrimination.

<Example 11> Discrimination of Mutant with K511A Mutation and Additional Mutation Introduced The mutant CS2-K511A, into which the mutations of I707L and E708K, as sites reported as a cold sensitive mutant with activity inhibited at a low temperature, were further introduced, was constructed according to the method of <Example 6>. The mutant was cultured and purified with purify of 95% or higher on SDS-PAGE as in <Experimental Example 2> and <Experimental Example 4>. The purified CS2-K511A Taq DNA polymerase was subjected to real-time PCR as in <Experimental Example 6>. In such a case, EGFR-ARMS-F was used as the forward primer. Under the PCR conditions, the CS2-K511A Taq DNA polymerase showed very high discrimination between matches and mismatches in the real-time PCR, compared with wild-type Taq DNA polymerase (Table 3 and FIG. 8).

INDUSTRIAL APPLICABILITY

The DNA polymerase mutants with enhanced discrimination of the present invention has enhanced base match and mismatch discrimination between a template and a primer while having maintained or enhanced polymerization activity, and thus can easily identify the presence or absence of a matched or mismatched mutation sites and the amplification or non-amplification, and therefore, the DNA polymerase mutants can easily detect alleles in a sample in which small amounts of multiple species are mixed, facilitating the detection of mutant genes in a sample containing small amount of mutations and can be widely used in genetic testing for agricultural, fishery, and livestock products and diagnosis in the medical field, and the like.

The present invention was made with the support of the Ministry of Agriculture, Food, and Rural Affairs, Republic of Korea (Project ID number: 1545019806, Project title: Development of real time PCR technology based on FenDEL for cultivar varieties identification).

What is claimed is:

1. A modified DNA polymerase, wherein the modified DNA polymerase comprises the sequence of SEQ ID NO: 1 with a modification, said modification comprising an amino acid mutation selected from the group consisting of K511A, K511R, R512K, K511A/R512K, and K511R/R512K relative to SEQ ID NO: 1; and wherein the modified DNA polymerase retains polymerization activity and exhibits enhanced discrimination of an allelic or genetic mutation compared to the DNA polymerase of SEQ ID NO: 1 without modification.

2. The modified DNA polymerase of claim 1, which further comprises a mutation at one or more positions selected from the group consisting of positions 497, 498, 499, 500, 501, 502, 503, 505, 506, 509, 510, 513, and 514 relative to the sequence of SEQ ID NO: 1.

3. The modified DNA polymerase of claim 1, which further comprises a mutation of I707L, E708K, or I707L/E708K.

4. The modified DNA polymerase of claim 1, which comprises three amino acid mutations K511A, I707L, and E708K.

5. A method for performing a real-time polymerase chain reaction to enhance the discrimination of an allelic or genetic mutation, the method comprising:

mixing a template DNA, an allele-specific primer or an amplification refractory mutation system (ARMS) primer, and the modified DNA polymerase of claim 1 to form a reaction mixture;

subjecting the reaction mixture to real-time polymerase chain reaction conditions; and detecting an amplification product to determine the presence or absence of the allelic or genetic mutation.

6. A polymerase chain reaction kit comprising the modified DNA polymerase of claim 1.

* * * * *

SEQUENCE LISTING

```
<160> NUMBER OF SEQ ID NOS: 106

<210> SEQ ID NO 1
<211> LENGTH: 832
<212> TYPE: PRT
<213> ORGANISM: Thermus Aquaticus

<400> SEQUENCE: 1

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240
```

```
Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
        435                 440                 445

Val Arg Leu Asp Val Ala Tyr Leu Arg Ala Leu Ser Leu Glu Val Ala
    450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
    610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655
```

-continued

```
Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830


<210> SEQ ID NO 2
<211> LENGTH: 834
<212> TYPE: PRT
<213> ORGANISM: Thermus sp.

<400> SEQUENCE: 2

Met Lys Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Phe Glu Ala Asp Asp Val Leu Ala Thr Leu Ala Lys
        115                 120                 125

Lys Ala Glu Arg Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205
```

```
Leu Lys Glu Trp Gly Ser Leu Glu Asn Ile Leu Lys Asn Leu Asp Arg
    210                 215                 220

Val Lys Pro Glu Ser Val Arg Glu Arg Ile Lys Ala His Leu Glu Asp
225                 230                 235                 240

Leu Lys Leu Ser Leu Glu Leu Ser Arg Val Arg Ser Asp Leu Pro Leu
                245                 250                 255

Glu Val Asp Phe Ala Arg Arg Arg Glu Pro Asp Arg Glu Gly Leu Arg
            260                 265                 270

Ala Phe Leu Glu Arg Leu Glu Phe Gly Ser Leu Leu His Glu Phe Gly
        275                 280                 285

Leu Leu Glu Ala Pro Ala Pro Leu Glu Glu Ala Pro Trp Pro Pro Pro
    290                 295                 300

Glu Gly Ala Phe Val Gly Phe Val Leu Ser Arg Pro Glu Pro Met Trp
305                 310                 315                 320

Ala Glu Leu Lys Ala Leu Ala Ala Cys Lys Glu Gly Arg Val His Arg
                325                 330                 335

Ala Lys Asp Pro Leu Ala Gly Leu Lys Asp Leu Lys Glu Val Arg Gly
            340                 345                 350

Leu Leu Ala Lys Asp Leu Ala Val Leu Ala Leu Arg Glu Gly Leu Asp
        355                 360                 365

Leu Ala Pro Ser Asp Asp Pro Met Leu Leu Ala Tyr Leu Leu Asp Pro
    370                 375                 380

Ser Asn Thr Thr Pro Glu Gly Val Ala Arg Arg Tyr Gly Gly Glu Trp
385                 390                 395                 400

Thr Glu Asp Ala Ala His Arg Ala Leu Leu Ala Glu Arg Leu Gln Gln
                405                 410                 415

Asn Leu Leu Glu Arg Leu Lys Gly Glu Glu Lys Leu Leu Trp Leu Tyr
            420                 425                 430

Gln Glu Val Glu Lys Pro Leu Ser Arg Val Leu Ala His Met Glu Ala
        435                 440                 445

Thr Gly Val Arg Leu Asp Val Ala Tyr Leu Lys Ala Leu Ser Leu Glu
    450                 455                 460

Leu Ala Glu Glu Ile Arg Arg Leu Glu Glu Glu Val Phe Arg Leu Ala
465                 470                 475                 480

Gly His Pro Phe Asn Leu Asn Ser Arg Asp Gln Leu Glu Arg Val Leu
                485                 490                 495

Phe Asp Glu Leu Arg Leu Pro Ala Leu Gly Lys Thr Gln Lys Thr Gly
            500                 505                 510

Lys Arg Ser Thr Ser Ala Ala Val Leu Glu Ala Leu Arg Glu Ala His
        515                 520                 525

Pro Ile Val Glu Lys Ile Leu Gln His Arg Glu Leu Thr Lys Leu Lys
    530                 535                 540

Asn Thr Tyr Val Asp Pro Leu Pro Gly Leu Val His Pro Arg Thr Gly
545                 550                 555                 560

Arg Leu His Thr Arg Phe Asn Gln Thr Ala Thr Ala Thr Gly Arg Leu
                565                 570                 575

Ser Ser Ser Asp Pro Asn Leu Gln Asn Ile Pro Ile Arg Thr Pro Leu
            580                 585                 590

Gly Gln Arg Ile Arg Arg Ala Phe Val Ala Glu Ala Gly Trp Ala Leu
        595                 600                 605

Val Ala Leu Asp Tyr Ser Gln Ile Glu Leu Arg Val Leu Ala His Leu
    610                 615                 620
```

-continued

Ser Gly Asp Glu Asn Leu Ile Arg Val Phe Gln Glu Gly Lys Asp Ile
625 630 635 640

His Thr Gln Thr Ala Ser Trp Met Phe Gly Val Ser Pro Glu Ala Val
645 650 655

Asp Pro Leu Met Arg Arg Ala Ala Lys Thr Val Asn Phe Gly Val Leu
660 665 670

Tyr Gly Met Ser Ala His Arg Leu Ser Gln Glu Leu Ala Ile Pro Tyr
675 680 685

Glu Glu Ala Val Ala Phe Ile Glu Arg Tyr Phe Gln Ser Phe Pro Lys
690 695 700

Val Arg Ala Trp Ile Glu Lys Thr Leu Glu Glu Gly Arg Lys Arg Gly
705 710 715 720

Tyr Val Glu Thr Leu Phe Gly Arg Arg Arg Tyr Val Pro Asp Leu Asn
725 730 735

Ala Arg Val Lys Ser Val Arg Glu Ala Ala Glu Arg Met Ala Phe Asn
740 745 750

Met Pro Val Gln Gly Thr Ala Ala Asp Leu Met Lys Leu Ala Met Val
755 760 765

Lys Leu Phe Pro His Leu Arg Glu Met Gly Ala Arg Met Leu Leu Gln
770 775 780

Val His Asp Glu Leu Leu Leu Glu Ala Pro Gln Ala Arg Ala Glu Glu
785 790 795 800

Val Ala Ala Leu Ala Lys Glu Ala Met Glu Lys Ala Tyr Pro Leu Ala
805 810 815

Val Pro Leu Glu Val Glu Val Gly Ile Gly Glu Asp Trp Leu Ser Ala
820 825 830

Lys Gly

<210> SEQ ID NO 3
<211> LENGTH: 501
<212> TYPE: DNA
<213> ORGANISM: Homo Sapiens

<400> SEQUENCE: 3
aaaatattcg ttttaagggt aaagaaaaaa gttaaaaaat ctatttacat aaaaaataag 60
aacactgatt tttgtgaata ctgggaacta tgaaaatact atagttgaga ccttcaatga 120
ctttctagta actcagcagc atctcagggc caaaaattta atcagtggaa aaatagcctc 180
aattcttacc atccacaaaa tggatccaga caactgttca aactgatggg acccactcca 240
tcgagatttc actgtagcta gaccaaaatc acctattttt actgtgaggt cttcatgaag 300
aaatatatct gaggtgtagt aagtaaagga aaacagtaga tctcattttc ctatcagagc 360
aagcattatg aagagtttag gtaagagatc taatttctat aattctgtaa tataatattc 420
tttaaaacat agtacttcat ctttcctctt agagtcaata agtatgtcta aaacaatgat 480
tagttctatt tagcctatat a 501

<210> SEQ ID NO 4
<211> LENGTH: 501
<212> TYPE: DNA
<213> ORGANISM: Homo sapiens

<400> SEQUENCE: 4
aaaatattcg ttttaagggt aaagaaaaaa gttaaaaaat ctatttacat aaaaaataag 60
aacactgatt tttgtgaata ctgggaacta tgaaaatact atagttgaga ccttcaatga 120
ctttctagta actcagcagc atctcagggc caaaaattta atcagtggaa aaatagcctc 180
aattcttacc atccacaaaa tggatccaga caactgttca aactgatggg acccactcca 240
tcgagatttc tctgtagcta gaccaaaatc acctattttt actgtgaggt cttcatgaag 300
aaatatatct gaggtgtagt aagtaaagga aaacagtaga tctcattttc ctatcagagc 360
aagcattatg aagagtttag gtaagagatc taatttctat aattctgtaa tataatattc 420
tttaaaacat agtacttcat ctttcctctt agagtcaata agtatgtcta aaacaatgat 480
tagttctatt tagcctatat a 501

<210> SEQ ID NO 5
<211> LENGTH: 448
<212> TYPE: DNA
<213> ORGANISM: Homo sapiens

<400> SEQUENCE: 5
cacgcacaca catatcccca tggcaaactc ttgctatccc aggagcgcag accgcatgtg 60
aggatcctgg ctccttatct cccctccccg tatctccctt ccctgattac ctttgcgatc 120
tgcacacacc agttgagcag gtactgggag ccaatattgt ctttgtgttc ccggacatag 180
tccaggaggc agccgaaggg catgagctgc gtgatgagct gcacggtgga ggtgaggcag 240
atgcccagca ggcggcacac gtgggggttg tccacgctgg ccatcacgta ggcttcctgg 300
agggagggag aggcacgtca gtgtggcttc gcatggtggc cagaaggagg ggcacatgga 360
ccccttccag gtgaagacgc atgaatgcga tcttgagttt caaaatacgt actcatggag 420
gaaaagctgt gcctgcaaaa gacctagc 448

<210> SEQ ID NO 6
<211> LENGTH: 448
<212> TYPE: DNA
<213> ORGANISM: Homo sapiens

<400> SEQUENCE: 6
cacgcacaca catatcccca tggcaaactc ttgctatccc aggagcgcag accgcatgtg 60
aggatcctgg ctccttatct cccctccccg tatctccctt ccctgattac ctttgcgatc 120
tgcacacacc agttgagcag gtactgggag ccaatattgt ctttgtgttc ccggacatag 180
tccaggaggc agccgaaggg catgagctgc atgatgagct gcacggtgga ggtgaggcag 240
atgcccagca ggcggcacac gtgggggttg tccacgctgg ccatcacgta ggcttcctgg 300
agggagggag aggcacgtca gtgtggcttc gcatggtggc cagaaggagg ggcacatgga 360
ccccttccag gtgaagacgc atgaatgcga tcttgagttt caaaatacgt actcatggag 420
gaaaagctgt gcctgcaaaa gacctagc 448

<210> SEQ ID NO 7
<211> LENGTH: 18
<212> TYPE: PRT
<213> ORGANISM: Thermus Aquaticus

<400> SEQUENCE: 7

Glu Leu Gly Leu Pro Ala Ile Gly Lys Thr Glu Lys Thr Gly Lys Arg
1 5 10 15

Ser Thr

<210> SEQ ID NO 8
<211> LENGTH: 30
<212> TYPE: DNA

<213> ORGANISM: Artificial Sequence
<220> FEATURE:
<223> OTHER INFORMATION: primer

<400> SEQUENCE: 8
tttgacgagc taagacttcc cgccatcggc 30

<210> SEQ ID NO 9
<211> LENGTH: 30
<212> TYPE: DNA
<213> ORGANISM: Artificial Sequence
<220> FEATURE:
<223> OTHER INFORMATION: primer

<400> SEQUENCE: 9
gccgatggcg ggaagtctta gctcgtcaaa 30

<210> SEQ ID NO 10
<211> LENGTH: 30
<212> TYPE: DNA
<213> ORGANISM: Artificial Sequence
<220> FEATURE:
<223> OTHER INFORMATION: primer

<400> SEQUENCE: 10
cccgccatcg gcgctacgga gaagaccggc 30

<210> SEQ ID NO 11
<211> LENGTH: 30
<212> TYPE: DNA
<213> ORGANISM: Artificial Sequence
<220> FEATURE:
<223> OTHER INFORMATION: primer

<400> SEQUENCE: 11
gccggtcttc tccgtagcgc cgatggcggg 30

<210> SEQ ID NO 12
<211> LENGTH: 30
<212> TYPE: DNA
<213> ORGANISM: Artificial Sequence
<220> FEATURE:
<223> OTHER INFORMATION: primer

<400> SEQUENCE: 12
cccgccatcg gcgaaacgga gaagaccggc 30

<210> SEQ ID NO 13
<211> LENGTH: 30
<212> TYPE: DNA
<213> ORGANISM: Artificial Sequence
<220> FEATURE:
<223> OTHER INFORMATION: primer

<400> SEQUENCE: 13
gccggtcttc tccgtttcgc cgatggcggg 30

<210> SEQ ID NO 14
<211> LENGTH: 30
<212> TYPE: DNA
<213> ORGANISM: Artificial Sequence
<220> FEATURE:
<223> OTHER INFORMATION: primer

<400> SEQUENCE: 14
cccgccatcg gctctacgga gaagaccggc 30

<210> SEQ ID NO 15
<211> LENGTH: 30
<212> TYPE: DNA
<213> ORGANISM: Artificial Sequence
<220> FEATURE:
<223> OTHER INFORMATION: primer

<400> SEQUENCE: 15
gccggtcttc tccgtagagc cgatggcggg 30

<210> SEQ ID NO 16
<211> LENGTH: 30
<212> TYPE: DNA
<213> ORGANISM: Artificial Sequence
<220> FEATURE:
<223> OTHER INFORMATION: primer

<400> SEQUENCE: 16
cccgccatcg gcggtacgga gaagaccggc 30

<210> SEQ ID NO 17
<211> LENGTH: 30
<212> TYPE: DNA
<213> ORGANISM: Artificial Sequence
<220> FEATURE:
<223> OTHER INFORMATION: primer

<400> SEQUENCE: 17
gccggtcttc tccgtaccgc cgatggcggg 30

<210> SEQ ID NO 18
<211> LENGTH: 30
<212> TYPE: DNA
<213> ORGANISM: Artificial Sequence
<220> FEATURE:
<223> OTHER INFORMATION: primer

<400> SEQUENCE: 18
cccgccatcg gcagaacgga gaagaccggc 30

<210> SEQ ID NO 19
<211> LENGTH: 30
<212> TYPE: DNA
<213> ORGANISM: Artificial Sequence
<220> FEATURE:
<223> OTHER INFORMATION: primer

<400> SEQUENCE: 19
gccggtcttc tccgttctgc cgatggcggg 30

<210> SEQ ID NO 20
<211> LENGTH: 30
<212> TYPE: DNA
<213> ORGANISM: Artificial Sequence
<220> FEATURE:
<223> OTHER INFORMATION: primer

<400> SEQUENCE: 20
cccgccatcg gcttcacgga gaagaccggc 30

<210> SEQ ID NO 21
<211> LENGTH: 30
<212> TYPE: DNA
<213> ORGANISM: Artificial Sequence
<220> FEATURE:

<223> OTHER INFORMATION: primer

<400> SEQUENCE: 21
gccggtcttc tccgtgaagc cgatggcggg 30

<210> SEQ ID NO 22
<211> LENGTH: 30
<212> TYPE: DNA
<213> ORGANISM: Artificial Sequence
<220> FEATURE:
<223> OTHER INFORMATION: primer

<400> SEQUENCE: 22
cccgccatcg gcattacgga gaagaccggc 30

<210> SEQ ID NO 23
<211> LENGTH: 30
<212> TYPE: DNA
<213> ORGANISM: Artificial Sequence
<220> FEATURE:
<223> OTHER INFORMATION: primer

<400> SEQUENCE: 23
gccggtcttc tccgtaatgc cgatggcggg 30

<210> SEQ ID NO 24
<211> LENGTH: 30
<212> TYPE: DNA
<213> ORGANISM: Artificial Sequence
<220> FEATURE:
<223> OTHER INFORMATION: primer

<400> SEQUENCE: 24
cccgccatcg gccttacgga gaagaccggc 30

<210> SEQ ID NO 25
<211> LENGTH: 30
<212> TYPE: DNA
<213> ORGANISM: Artificial Sequence
<220> FEATURE:
<223> OTHER INFORMATION: primer

<400> SEQUENCE: 25
gccggtcttc tccgtaaggc cgatggcggg 30

<210> SEQ ID NO 26
<211> LENGTH: 30
<212> TYPE: DNA
<213> ORGANISM: Artificial Sequence
<220> FEATURE:
<223> OTHER INFORMATION: primer

<400> SEQUENCE: 26
cccgccatcg gcatgacgga gaagaccggc 30

<210> SEQ ID NO 27
<211> LENGTH: 30
<212> TYPE: DNA
<213> ORGANISM: Artificial Sequence
<220> FEATURE:
<223> OTHER INFORMATION: primer

<400> SEQUENCE: 27
gccggtcttc tccgtcatgc cgatggcggg 30

<210> SEQ ID NO 28
<211> LENGTH: 30
<212> TYPE: DNA
<213> ORGANISM: Artificial Sequence
<220> FEATURE:
<223> OTHER INFORMATION: primer

<400> SEQUENCE: 28
cccgccatcg gctggacgga gaagaccggc 30

<210> SEQ ID NO 29
<211> LENGTH: 30
<212> TYPE: DNA
<213> ORGANISM: Artificial Sequence
<220> FEATURE:
<223> OTHER INFORMATION: primer

<400> SEQUENCE: 29
gccggtcttc tccgtccagc cgatggcggg 30

<210> SEQ ID NO 30
<211> LENGTH: 30
<212> TYPE: DNA
<213> ORGANISM: Artificial Sequence
<220> FEATURE:
<223> OTHER INFORMATION: primer

<400> SEQUENCE: 30
atcggcaaga cggctaagac cggcaagcgc 30

<210> SEQ ID NO 31
<211> LENGTH: 30
<212> TYPE: DNA
<213> ORGANISM: Artificial Sequence
<220> FEATURE:
<223> OTHER INFORMATION: primer

<400> SEQUENCE: 31
gcgcttgccg gtcttagccg tcttgccgat 30

<210> SEQ ID NO 32
<211> LENGTH: 30
<212> TYPE: DNA
<213> ORGANISM: Artificial Sequence
<220> FEATURE:
<223> OTHER INFORMATION: primer

<400> SEQUENCE: 32
atcggcaaga cgaagaagac cggcaagcgc 30

<210> SEQ ID NO 33
<211> LENGTH: 30
<212> TYPE: DNA
<213> ORGANISM: Artificial Sequence
<220> FEATURE:
<223> OTHER INFORMATION: primer

<400> SEQUENCE: 33
gcgcttgccg gtcttcttcg tcttgccgat 30

<210> SEQ ID NO 34
<211> LENGTH: 30
<212> TYPE: DNA
<213> ORGANISM: Artificial Sequence
<220> FEATURE:
<223> OTHER INFORMATION: primer

<400> SEQUENCE: 34
atcggcaaga cgtctaagac cggcaagcgc 30

<210> SEQ ID NO 35
<211> LENGTH: 30
<212> TYPE: DNA
<213> ORGANISM: Artificial Sequence
<220> FEATURE:
<223> OTHER INFORMATION: primer

<400> SEQUENCE: 35
gcgcttgccg gtcttagacg tcttgccgat 30

<210> SEQ ID NO 36
<211> LENGTH: 30
<212> TYPE: DNA
<213> ORGANISM: Artificial Sequence
<220> FEATURE:
<223> OTHER INFORMATION: primer

<400> SEQUENCE: 36
atcggcaaga cgggtaagac cggcaagcgc 30

<210> SEQ ID NO 37
<211> LENGTH: 30
<212> TYPE: DNA
<213> ORGANISM: Artificial Sequence
<220> FEATURE:
<223> OTHER INFORMATION: primer

<400> SEQUENCE: 37
gcgcttgccg gtcttacccg tcttgccgat 30

<210> SEQ ID NO 38
<211> LENGTH: 30
<212> TYPE: DNA
<213> ORGANISM: Artificial Sequence
<220> FEATURE:
<223> OTHER INFORMATION: primer

<400> SEQUENCE: 38
atcggcaaga cgcagaagac cggcaagcgc 30

<210> SEQ ID NO 39
<211> LENGTH: 30
<212> TYPE: DNA
<213> ORGANISM: Artificial Sequence
<220> FEATURE:
<223> OTHER INFORMATION: primer

<400> SEQUENCE: 39
gcgcttgccg gtcttctgcg tcttgccgat 30

<210> SEQ ID NO 40
<211> LENGTH: 30
<212> TYPE: DNA
<213> ORGANISM: Artificial Sequence
<220> FEATURE:
<223> OTHER INFORMATION: primer

<400> SEQUENCE: 40
gagaagaccg gcgctcgctc caccagcgcc 30

<210> SEQ ID NO 41
<211> LENGTH: 30

<212> TYPE: DNA
<213> ORGANISM: Artificial Sequence
<220> FEATURE:
<223> OTHER INFORMATION: primer

<400> SEQUENCE: 41
ggcgctggtg gagcgagcgc cggtcttctc 30

<210> SEQ ID NO 42
<211> LENGTH: 30
<212> TYPE: DNA
<213> ORGANISM: Artificial Sequence
<220> FEATURE:
<223> OTHER INFORMATION: primer

<400> SEQUENCE: 42
gagaagaccg gcagacgctc caccagcgcc 30

<210> SEQ ID NO 43
<211> LENGTH: 30
<212> TYPE: DNA
<213> ORGANISM: Artificial Sequence
<220> FEATURE:
<223> OTHER INFORMATION: primer

<400> SEQUENCE: 43
ggcgctggtg gagcgtctgc cggtcttctc 30

<210> SEQ ID NO 44
<211> LENGTH: 30
<212> TYPE: DNA
<213> ORGANISM: Artificial Sequence
<220> FEATURE:
<223> OTHER INFORMATION: primer

<400> SEQUENCE: 44
gagaagaccg gcgaacgctc caccagcgcc 30

<210> SEQ ID NO 45
<211> LENGTH: 30
<212> TYPE: DNA
<213> ORGANISM: Artificial Sequence
<220> FEATURE:
<223> OTHER INFORMATION: primer

<400> SEQUENCE: 45
ggcgctggtg gagcgttcgc cggtcttctc 30

<210> SEQ ID NO 46
<211> LENGTH: 30
<212> TYPE: DNA
<213> ORGANISM: Artificial Sequence
<220> FEATURE:
<223> OTHER INFORMATION: primer

<400> SEQUENCE: 46
gagaagaccg gctctcgctc caccagcgcc 30

<210> SEQ ID NO 47
<211> LENGTH: 30
<212> TYPE: DNA
<213> ORGANISM: Artificial Sequence
<220> FEATURE:
<223> OTHER INFORMATION: primer

<400> SEQUENCE: 47
ggcgctggtg gagcgagagc cggtcttctc 30

<210> SEQ ID NO 48
<211> LENGTH: 30
<212> TYPE: DNA
<213> ORGANISM: Artificial Sequence
<220> FEATURE:
<223> OTHER INFORMATION: primer

<400> SEQUENCE: 48
gagaagaccg gcggtcgctc caccagcgcc 30

<210> SEQ ID NO 49
<211> LENGTH: 30
<212> TYPE: DNA
<213> ORGANISM: Artificial Sequence
<220> FEATURE:
<223> OTHER INFORMATION: primer

<400> SEQUENCE: 49
ggcgctggtg gagcgaccgc cggtcttctc 30

<210> SEQ ID NO 50
<211> LENGTH: 30
<212> TYPE: DNA
<213> ORGANISM: Artificial Sequence
<220> FEATURE:
<223> OTHER INFORMATION: primer

<400> SEQUENCE: 50
gagaagaccg gcgttcgctc caccagcgcc 30

<210> SEQ ID NO 51
<211> LENGTH: 30
<212> TYPE: DNA
<213> ORGANISM: Artificial Sequence
<220> FEATURE:
<223> OTHER INFORMATION: primer

<400> SEQUENCE: 51
ggcgctggtg gagcgaacgc cggtcttctc 30

<210> SEQ ID NO 52
<211> LENGTH: 30
<212> TYPE: DNA
<213> ORGANISM: Artificial Sequence
<220> FEATURE:
<223> OTHER INFORMATION: primer

<400> SEQUENCE: 52
gagaagaccg gcattcgctc caccagcgcc 30

<210> SEQ ID NO 53
<211> LENGTH: 30
<212> TYPE: DNA
<213> ORGANISM: Artificial Sequence
<220> FEATURE:
<223> OTHER INFORMATION: primer

<400> SEQUENCE: 53
ggcgctggtg gagcgaatgc cggtcttctc 30

<210> SEQ ID NO 54

<211> LENGTH: 30
<212> TYPE: DNA
<213> ORGANISM: Artificial Sequence
<220> FEATURE:
<223> OTHER INFORMATION: primer

<400> SEQUENCE: 54
gagaagaccg gccttcgctc caccagcgcc 30

<210> SEQ ID NO 55
<211> LENGTH: 30
<212> TYPE: DNA
<213> ORGANISM: Artificial Sequence
<220> FEATURE:
<223> OTHER INFORMATION: primer

<400> SEQUENCE: 55
ggcgctggtg gagcgaaggc cggtcttctc 30

<210> SEQ ID NO 56
<211> LENGTH: 30
<212> TYPE: DNA
<213> ORGANISM: Artificial Sequence
<220> FEATURE:
<223> OTHER INFORMATION: primer

<400> SEQUENCE: 56
gagaagaccg gcatgcgctc caccagcgcc 30

<210> SEQ ID NO 57
<211> LENGTH: 30
<212> TYPE: DNA
<213> ORGANISM: Artificial Sequence
<220> FEATURE:
<223> OTHER INFORMATION: primer

<400> SEQUENCE: 57
ggcgctggtg gagcgcatgc cggtcttctc 30

<210> SEQ ID NO 58
<211> LENGTH: 30
<212> TYPE: DNA
<213> ORGANISM: Artificial Sequence
<220> FEATURE:
<223> OTHER INFORMATION: primer

<400> SEQUENCE: 58
gagaagaccg gcttccgctc caccagcgcc 30

<210> SEQ ID NO 59
<211> LENGTH: 30
<212> TYPE: DNA
<213> ORGANISM: Artificial Sequence
<220> FEATURE:
<223> OTHER INFORMATION: primer

<400> SEQUENCE: 59
ggcgctggtg gagcggaagc cggtcttctc 30

<210> SEQ ID NO 60
<211> LENGTH: 30
<212> TYPE: DNA
<213> ORGANISM: Artificial Sequence
<220> FEATURE:
<223> OTHER INFORMATION: primer

<400> SEQUENCE: 60
gagaagaccg gctatcgctc caccagcgcc 30

<210> SEQ ID NO 61
<211> LENGTH: 30
<212> TYPE: DNA
<213> ORGANISM: Artificial Sequence
<220> FEATURE:
<223> OTHER INFORMATION: primer

<400> SEQUENCE: 61
ggcgctggtg gagcgatagc cggtcttctc 30

<210> SEQ ID NO 62
<211> LENGTH: 30
<212> TYPE: DNA
<213> ORGANISM: Artificial Sequence
<220> FEATURE:
<223> OTHER INFORMATION: primer

<400> SEQUENCE: 62
gagaagaccg gctggcgctc caccagcgcc 30

<210> SEQ ID NO 63
<211> LENGTH: 30
<212> TYPE: DNA
<213> ORGANISM: Artificial Sequence
<220> FEATURE:
<223> OTHER INFORMATION: primer

<400> SEQUENCE: 63
ggcgctggtg gagcgccagc cggtcttctc 30

<210> SEQ ID NO 64
<211> LENGTH: 30
<212> TYPE: DNA
<213> ORGANISM: Artificial Sequence
<220> FEATURE:
<223> OTHER INFORMATION: primer

<400> SEQUENCE: 64
aagaccggca aggcctccac cagcgccgcc 30

<210> SEQ ID NO 65
<211> LENGTH: 30
<212> TYPE: DNA
<213> ORGANISM: Artificial Sequence
<220> FEATURE:
<223> OTHER INFORMATION: primer

<400> SEQUENCE: 65
ggcggcgctg gtggaggcct tgccggtctt 30

<210> SEQ ID NO 66
<211> LENGTH: 30
<212> TYPE: DNA
<213> ORGANISM: Artificial Sequence
<220> FEATURE:
<223> OTHER INFORMATION: primer

<400> SEQUENCE: 66
aagaccggca aggaatccac cagcgccgcc 30

<210> SEQ ID NO 67

<211> LENGTH: 30
<212> TYPE: DNA
<213> ORGANISM: Artificial Sequence
<220> FEATURE:
<223> OTHER INFORMATION: primer

<400> SEQUENCE: 67
ggcggcgctg gtggattcct tgccggtctt 30

<210> SEQ ID NO 68
<211> LENGTH: 30
<212> TYPE: DNA
<213> ORGANISM: Artificial Sequence
<220> FEATURE:
<223> OTHER INFORMATION: primer

<400> SEQUENCE: 68
aagaccggca agtcttccac cagcgccgcc 30

<210> SEQ ID NO 69
<211> LENGTH: 30
<212> TYPE: DNA
<213> ORGANISM: Artificial Sequence
<220> FEATURE:
<223> OTHER INFORMATION: primer

<400> SEQUENCE: 69
ggcggcgctg gtggaagact tgccggtctt 30

<210> SEQ ID NO 70
<211> LENGTH: 30
<212> TYPE: DNA
<213> ORGANISM: Artificial Sequence
<220> FEATURE:
<223> OTHER INFORMATION: primer

<400> SEQUENCE: 70
aagaccggca agggttccac cagcgccgcc 30

<210> SEQ ID NO 71
<211> LENGTH: 30
<212> TYPE: DNA
<213> ORGANISM: Artificial Sequence
<220> FEATURE:
<223> OTHER INFORMATION: primer

<400> SEQUENCE: 71
ggcggcgctg gtggaaccct tgccggtctt 30

<210> SEQ ID NO 72
<211> LENGTH: 30
<212> TYPE: DNA
<213> ORGANISM: Artificial Sequence
<220> FEATURE:
<223> OTHER INFORMATION: primer

<400> SEQUENCE: 72
aagaccggca agaagtccac cagcgccgcc 30

<210> SEQ ID NO 73
<211> LENGTH: 30
<212> TYPE: DNA
<213> ORGANISM: Artificial Sequence
<220> FEATURE:
<223> OTHER INFORMATION: primer

<400> SEQUENCE: 73
ggcggcgctg gtggacttct tgccggtctt 30

<210> SEQ ID NO 74
<211> LENGTH: 30
<212> TYPE: DNA
<213> ORGANISM: Artificial Sequence
<220> FEATURE:
<223> OTHER INFORMATION: primer

<400> SEQUENCE: 74
aagaccggca agttctccac cagcgccgcc 30

<210> SEQ ID NO 75
<211> LENGTH: 30
<212> TYPE: DNA
<213> ORGANISM: Artificial Sequence
<220> FEATURE:
<223> OTHER INFORMATION: primer

<400> SEQUENCE: 75
ggcggcgctg gtggagaact tgccggtctt 30

<210> SEQ ID NO 76
<211> LENGTH: 30
<212> TYPE: DNA
<213> ORGANISM: Artificial Sequence
<220> FEATURE:
<223> OTHER INFORMATION: primer

<400> SEQUENCE: 76
aagaccggca agatttccac cagcgccgcc 30

<210> SEQ ID NO 77
<211> LENGTH: 30
<212> TYPE: DNA
<213> ORGANISM: Artificial Sequence
<220> FEATURE:
<223> OTHER INFORMATION: primer

<400> SEQUENCE: 77
ggcggcgctg gtggaaatct tgccggtctt 30

<210> SEQ ID NO 78
<211> LENGTH: 30
<212> TYPE: DNA
<213> ORGANISM: Artificial Sequence
<220> FEATURE:
<223> OTHER INFORMATION: primer

<400> SEQUENCE: 78
aagaccggca agctttccac cagcgccgcc 30

<210> SEQ ID NO 79
<211> LENGTH: 30
<212> TYPE: DNA
<213> ORGANISM: Artificial Sequence
<220> FEATURE:
<223> OTHER INFORMATION: primer

<400> SEQUENCE: 79
ggcggcgctg gtggaaagct tgccggtctt 30

<210> SEQ ID NO 80

<211> LENGTH: 30
<212> TYPE: DNA
<213> ORGANISM: Artificial Sequence
<220> FEATURE:
<223> OTHER INFORMATION: primer

<400> SEQUENCE: 80
aagaccggca agatgtccac cagcgccgcc 30

<210> SEQ ID NO 81
<211> LENGTH: 30
<212> TYPE: DNA
<213> ORGANISM: Artificial Sequence
<220> FEATURE:
<223> OTHER INFORMATION: primer

<400> SEQUENCE: 81
ggcggcgctg gtggacatct tgccggtctt 30

<210> SEQ ID NO 82
<211> LENGTH: 30
<212> TYPE: DNA
<213> ORGANISM: Artificial Sequence
<220> FEATURE:
<223> OTHER INFORMATION: primer

<400> SEQUENCE: 82
aagaccggca aggtttccac cagcgccgcc 30

<210> SEQ ID NO 83
<211> LENGTH: 30
<212> TYPE: DNA
<213> ORGANISM: Artificial Sequence
<220> FEATURE:
<223> OTHER INFORMATION: primer

<400> SEQUENCE: 83
ggcggcgctg gtggaaacct tgccggtctt 30

<210> SEQ ID NO 84
<211> LENGTH: 30
<212> TYPE: DNA
<213> ORGANISM: Artificial Sequence
<220> FEATURE:
<223> OTHER INFORMATION: primer

<400> SEQUENCE: 84
aagaccggca agtggtccac cagcgccgcc 30

<210> SEQ ID NO 85
<211> LENGTH: 30
<212> TYPE: DNA
<213> ORGANISM: Artificial Sequence
<220> FEATURE:
<223> OTHER INFORMATION: primer

<400> SEQUENCE: 85
ggcggcgctg gtggaccact tgccggtctt 30

<210> SEQ ID NO 86
<211> LENGTH: 30
<212> TYPE: DNA
<213> ORGANISM: Artificial Sequence
<220> FEATURE:
<223> OTHER INFORMATION: primer

<400> SEQUENCE: 86
aagaccggca agtattccac cagcgccgcc 30

<210> SEQ ID NO 87
<211> LENGTH: 30
<212> TYPE: DNA
<213> ORGANISM: Artificial Sequence
<220> FEATURE:
<223> OTHER INFORMATION: primer

<400> SEQUENCE: 87
ggcggcgctg gtggaatact tgccggtctt 30

<210> SEQ ID NO 88
<211> LENGTH: 30
<212> TYPE: DNA
<213> ORGANISM: Artificial Sequence
<220> FEATURE:
<223> OTHER INFORMATION: primer

<400> SEQUENCE: 88
aagaccggca agcactccac cagcgccgcc 30

<210> SEQ ID NO 89
<211> LENGTH: 30
<212> TYPE: DNA
<213> ORGANISM: Artificial Sequence
<220> FEATURE:
<223> OTHER INFORMATION: primer

<400> SEQUENCE: 89
ggcggcgctg gtggagtgct tgccggtctt 30

<210> SEQ ID NO 90
<211> LENGTH: 30
<212> TYPE: DNA
<213> ORGANISM: Artificial Sequence
<220> FEATURE:
<223> OTHER INFORMATION: primer

<400> SEQUENCE: 90
gtgcgggcct ggcttgagaa gaccctggag 30

<210> SEQ ID NO 91
<211> LENGTH: 30
<212> TYPE: DNA
<213> ORGANISM: Artificial Sequence
<220> FEATURE:
<223> OTHER INFORMATION: primer

<400> SEQUENCE: 91
ctccagggtc ttctcaagcc aggcccgcac 30

<210> SEQ ID NO 92
<211> LENGTH: 30
<212> TYPE: DNA
<213> ORGANISM: Artificial Sequence
<220> FEATURE:
<223> OTHER INFORMATION: primer

<400> SEQUENCE: 92
cgggcctgga ttaagaagac cctggaggag 30

<210> SEQ ID NO 93

<211> LENGTH: 30
<212> TYPE: DNA
<213> ORGANISM: Artificial Sequence
<220> FEATURE:
<223> OTHER INFORMATION: primer

<400> SEQUENCE: 93
ctcctccagg gtcttcttaa tccaggcccg 30

<210> SEQ ID NO 94
<211> LENGTH: 24
<212> TYPE: DNA
<213> ORGANISM: Artificial Sequence
<220> FEATURE:
<223> OTHER INFORMATION: primer

<400> SEQUENCE: 94
gggacccact ccatcgagat ttct 24

<210> SEQ ID NO 95
<211> LENGTH: 27
<212> TYPE: DNA
<213> ORGANISM: Artificial Sequence
<220> FEATURE:
<223> OTHER INFORMATION: primer

<400> SEQUENCE: 95
aactcttcat aatgcttgct ctgatag 27

<210> SEQ ID NO 96
<211> LENGTH: 19
<212> TYPE: DNA
<213> ORGANISM: Artificial Sequence
<220> FEATURE:
<223> OTHER INFORMATION: probe

<400> SEQUENCE: 96
ctgtgaggtc ttcatgaag 19

<210> SEQ ID NO 97
<211> LENGTH: 21
<212> TYPE: DNA
<213> ORGANISM: Artificial Sequence
<220> FEATURE:
<223> OTHER INFORMATION: primer

<400> SEQUENCE: 97
agccgaaggg catgagctgc a 21

<210> SEQ ID NO 98
<211> LENGTH: 21
<212> TYPE: DNA
<213> ORGANISM: Artificial Sequence
<220> FEATURE:
<223> OTHER INFORMATION: primer

<400> SEQUENCE: 98
agccgaaggg catgagctac a 21

<210> SEQ ID NO 99
<211> LENGTH: 24
<212> TYPE: DNA
<213> ORGANISM: Artificial Sequence
<220> FEATURE:
<223> OTHER INFORMATION: primer

<400> SEQUENCE: 99
agtgtggaca acccccacgt gtgc 24

<210> SEQ ID NO 100
<211> LENGTH: 20
<212> TYPE: DNA
<213> ORGANISM: Artificial Sequence
<220> FEATURE:
<223> OTHER INFORMATION: probe

<400> SEQUENCE: 100
cggtggaggt gaggcagatg 20

<210> SEQ ID NO 101
<211> LENGTH: 59
<212> TYPE: PRT
<213> ORGANISM: Thermus maritima

<400> SEQUENCE: 101

Ala Gly Glu Pro Phe Asn Ile Asn Ser Pro Lys Gln Val Ser Arg Ile
1 5 10 15

Leu Phe Glu Lys Leu Gly Ile Lys Pro Arg Gly Lys Thr Thr Lys Thr
20 25 30

Gly Asp Tyr Ser Thr Arg Ile Glu Val Leu Glu Glu Leu Ala Gly Glu
35 40 45

His Glu Ile Ile Pro Leu Ile Leu Glu Tyr Arg
50 55

<210> SEQ ID NO 102
<211> LENGTH: 58
<212> TYPE: PRT
<213> ORGANISM: Escherichia coli

<400> SEQUENCE: 102

Ala Gly Glu Glu Phe Asn Leu Ser Ser Thr Lys Gln Leu Gln Thr Ile
1 5 10 15

Leu Phe Glu Lys Gln Gly Ile Lys Pro Leu Lys Lys Thr Pro Gly Gly
20 25 30

Ala Pro Ser Thr Ser Glu Glu Val Leu Glu Glu Leu Ala Leu Asp Tyr
35 40 45

Pro Leu Pro Lys Val Ile Leu Glu Tyr Arg
50 55

<210> SEQ ID NO 103
<211> LENGTH: 57
<212> TYPE: PRT
<213> ORGANISM: Bacillus caldotenax

<400> SEQUENCE: 103

Ala Gly Gln Glu Phe Asn Ile Asn Ser Pro Lys Gln Leu Gly Val Ile
1 5 10 15

Leu Phe Glu Lys Leu Gln Leu Pro Val Leu Lys Lys Ser Lys Thr Gly
20 25 30

Tyr Ser Thr Ser Ala Asp Val Leu Glu Lys Leu Ala Pro Tyr His Glu
35 40 45

Ile Val Glu Asn Ile Leu Gln His Tyr
50 55

<210> SEQ ID NO 104

```
<211> LENGTH: 57
<212> TYPE: PRT
<213> ORGANISM: Geobacillus stearothermophilus

<400> SEQUENCE: 104

Ala Gly Gln Glu Phe Asn Ile Asn Ser Pro Lys Gln Leu Gly Thr Val
1               5                   10                  15

Leu Phe Asp Lys Leu Gln Leu Pro Val Leu Lys Lys Thr Lys Thr Gly
            20                  25                  30

Tyr Ser Thr Ser Ala Asp Val Leu Glu Lys Leu Ala Pro His His Glu
        35                  40                  45

Ile Val Glu His Ile Leu His Tyr Arg
    50                  55


<210> SEQ ID NO 105
<211> LENGTH: 21
<212> TYPE: DNA
<213> ORGANISM: Artificial Sequence
<220> FEATURE:
<223> OTHER INFORMATION: primer

<400> SEQUENCE: 105

ggtgc tttat gactc tgccg c                                            21


<210> SEQ ID NO 106
<211> LENGTH: 19
<212> TYPE: DNA
<213> ORGANISM: Artificial Sequence
<220> FEATURE:
<223> OTHER INFORMATION: primer

<400> SEQUENCE: 106

agcgc ccttc ctggt atgc                                               19
```